United States Patent
Fliss et al.

(10) Patent No.: US 6,605,433 B1
(45) Date of Patent: Aug. 12, 2003

(54) MITOCHONDRIAL DOSIMETER

(75) Inventors: Makiko Fliss, Columbia, MD (US); David Sidransky, Baltimore, MD (US); Jin Jen, Brookville, MD (US); Kornelia Polyak, Brookline, MA (US); Bert Vogelstein, Baltimore, MD (US); Kenneth W. Kinzler, BelAir, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/525,906

(22) Filed: Mar. 15, 2000

Related U.S. Application Data

(63) Continuation-in-part of application No. 09/377,856, filed on Aug. 20, 1999.
(60) Provisional application No. 60/097,307, filed on Aug. 20, 1998.

(51) Int. Cl.[7] ............... C12Q 1/68; C12P 19/34; C07H 21/02
(52) U.S. Cl. ............... 435/6; 435/91.1; 435/91.2; 536/23.1; 536/24.3; 536/24.33; 436/504
(58) Field of Search ............... 435/6, 91.1, 91.2; 536/23.1, 24.3, 24.33; 436/504; 935/77, 78

(56) References Cited

U.S. PATENT DOCUMENTS

| | | | | |
|---|---|---|---|---|
| 5,935,787 | A | * | 8/1999 | Sidransky ............... 435/6 |
| 6,025,127 | A | * | 2/2000 | Sidransky ............... 435/6 |

FOREIGN PATENT DOCUMENTS

| | | |
|---|---|---|
| WO | WO-00/11219 | 3/2000 |

OTHER PUBLICATIONS

Alonso et al. Detection of somatic mutations in the mitochondrial DNA control region of colorectal and gastric tumors by heteroduplex and single–strand conformation analysis. Electrophoresis vol. 18, pp. 682–685, May 1997.*
Chee et al. Accessing Genetic information with high density DNA arrays. Science, vol. 274, pp. 610–614, Oct. 1996.*
Taira et al, "Tumor associated mutations of rat mitochondrial transfer RNA genes" Nucleic Acids Research (1983) 11(6):1635–1643.*
Burgart et al, "Somatic mitochondrial mutation in gastic cancer", American J. Pathol. (1995) 147(4):1105–1111.*
WALLACE, Science, 283:1482–1488 (1999).
Bianchi et al, Cytogenetics and Cell Genetics, vol. 71(1), pp. 99–103 (1995).
Tamura et al, European Journal of Cancer, vol. 35(2), pp. 316–319 (1999).
Chin–San et al, Envirnmental and Molecular Mutagenesis, vol. 30(1), pp. 47–55 (1997).
Ballinger et al, Cancer Research, vol. 56(24), pp. 5692–5697 (1996).
Database EMBL, H. Sapiens CpG Island DNA Genomic Msel Fragment, Database Accession No. Z56152, XP002211247 (Oct. 17, 1995).

* cited by examiner

*Primary Examiner*—Jeffrey Fredman
(74) *Attorney, Agent, or Firm*—Banner & Witcoff, Ltd.

(57) ABSTRACT

Mitochondrial mutations occur as a product of contact of a person with an environmental pollutant. Mitochondrial mutations are readily detectable in body fluids. Measurement of mitochondrial mutations in body fluids can be used as a dosimeter to monitor exposure to the environmental pollutant. Mitochondrial mutations can also be detected in cancer patients. Probes and primers containing mutant mitochondrial sequences can be used to monitor patient condition.

54 Claims, 8 Drawing Sheets

MITOCHONDRIAL DOSIMETER

This application is a continuation-in-part of application Ser. No. 09/377,856 filed Aug. 20, 1999, which claims priority to provisional application Ser. No. 60/097,307 filed Aug. 20, 1998. The disclosure of these prior applications is expressly incorporated herein.

The U.S. Government retains certain rights in this invention due to funding as provided by grant CA43460 awarded by the National Institutes of Health.

TECHNICAL FIELD OF THE INVENTION

This invention is related to the field of environmental toxicology, in particular to methods for measuring the effects of environmental toxins.

BACKGROUND OF THE INVENTION

The human mitochondrial (mt) genome is small (16.5 kb) and encodes 13 respiratory chain subunits, 22 tRNAs and two rRNAs. Mitochondrial DNA is present at extremely high levels ($10^3$–$10^4$ copies per cell) and the vast majority of these copies are identical (homoplasmic) at birth (1). Expression of the entire complement of mt genes is required to maintain proper function of the organelle, suggesting that even slight alterations in DNA sequences could have profound effects (2). It is generally accepted that mtDNA mutations are generated endogenously during oxidative phosphorylation via pathways involving reactive oxygen species (ROS), but they can also be generated by external carcinogens or environmental toxins. These mutations may accumulate partially because mitochondria lack protective histones and highly efficient DNA repair mechanisms as seen in the nucleus (3). Recently several mtDNA mutations were found specifically in human colorectal cancer (4).

SUMMARY OF THE INVENTION

It is an object of the present invention to provide methods of monitoring exposure of a person to an environmental pollutant.

It is another object of the present invention to provide a kit for monitoring exposure of a person to environmental pollutants.

It is an object of the invention to provide methods to aid in the detection of cancer or metastasis.

It is an object of the invention to provide probes and primers for detecting mitochondrial mutations.

It is an object of the invention to provide a method to aid in detecting the presence of tumor cells in a patient.

These and other objects of the invention are achieved by providing one or more of the embodiments described below. In one embodiment a method is provided for monitoring exposure of a person to an environmental pollutant. The presence of one or more mutations in mitochondrial DNA (mtDNA) in a body fluid of a person exposed to an environmental pollutant is determined at two or more time points. The amounts of mutations in mtDNA at different time points are compared. The amount of mutations correlates with amount of exposure to the environmental pollutant.

According to another embodiment another method is provided for monitoring exposure of a person to an environmental pollutant. The prevalence of one or more mutations in mitochondrial DNA (mtDNA) in a body fluid of a person exposed to an environmental pollutant is measured. A measured prevalence of one or more mutations in mtDNA of greater than 1% indicates clonal expansion of cells which harbor the one or more mutations in the person.

According to still another embodiment of the invention a method is provided for monitoring exposure of a person to an environmental pollutant. One or more mutations in a D-loop of mitochondrial DNA (mtDNA) in a body fluid of a person exposed to an environmental pollutant are measured. The number of mutations in mtDNA correlates with exposure to the environmental pollutant.

According to yet another embodiment of the invention a kit is provided. The kit comprises one or more primers which hybridize to a mitochondrial D-loop for making a primer extension product. In addition, the kit contains written material identifying mutations which are found in the D-loop as a result of exposure to one or more environmental pollutants.

According to another embodiment of the invention an oligonucleotide probe is provided. The probe comprises a sequence of at least 10 contiguous nucleotides of a human mitochondrial genome. The probe can optionally contain at least 12, 14, 16, 18, 20, 22, 24, 26, or 30 such contiguous nucleotides. The oligonucleotide comprises a mutation selected from the group consisting of: a mutation selected from the group consisting of: T→C at nucleotide 114; ΔC at nucleotide 302; C→A at nucleotide 386; insert T at nucleotide 16189; A→C at nucleotide 16265; A→T at nucleotide 16532; C→T at nucleotide 150; T→C at nucleotide 195; ΔC at nucleotide 302; C→A at nucleotide 16183; C→T at nucleotide 16187; T→C at nucleotide 16519; G→A at nucleotide 16380; G→A at nucleotide 75; insert C at nucleotide 302; insert CG at nucleotide 514; T→C at nucleotide 16172; C→T at nucleotide 16292; A→G at nucleotide 16300; A→G at nucleotide 10792; C→T at nucleotide 10793; C→T at nucleotide 10822; A→G at nucleotide 10978; A→G at nucleotide 11065; G→A at nucleotide 11518; C→T at nucleotide 12049; T→C at nucleotide 10966; G→A at nucleotide 11150; G→A at nucleotide 2056; T→C at nucleotide 2445; T→C at nucleotide 2664; T→C at nucleotide 10071; T→C at nucleotide 10321; T→C at nucleotide 12519; Δ 7 amino acids at nucleotide 15642; G→A at nucleotide 5521; G→A at nucleotide 12345; T→C substitution at position 710; T→C substitution at position 1738; T→C substitution at position 3308; G→A substitution at position 8009; G→A substitution at position 14985; T→C substitution at position 15572; G→A substitution at position 9949; T→C substitution at position 10563; G→A substitution at position 6264; A insertion at position 12418; T→C substitution at position 1967; T→A substitution at position 2299; and G→A at nucleotide 3054.

According to another aspect of the invention an oligonucleotide primer is provided. It comprises a sequence of at least 10 contiguous nucleotides of a human mitochondrial genome. The primer can optionally contain at least 12, 14, 16, 18, 20, 22, 24, 26, or 30 such contiguous nucleotides. The oligonucleotide comprises a mutation selected from the group consisting of: a mutation selected from the group consisting of: T→C at nucleotide 114; ΔC at nucleotide 302; C→A at nucleotide 386; insert T at nucleotide 16189; A→C at nucleotide 16265; A→T at nucleotide 16532; C→T at nucleotide 150; T→C at nucleotide 195; ΔC at nucleotide 302; C→A at nucleotide 16183; C→T at nucleotide 16187; T→C at nucleotide 16519; G→A at nucleotide 16380; G→A at nucleotide 75; insert C at nucleotide 302; insert CG at nucleotide 514; T→C at nucleotide 16172; C→T at nucleotide 16292; A→G at nucleotide 16300; A→G at nucleotide 10792; C→T at nucleotide 10793; C→T at nucleotide 10822; A→G at nucleotide 10978; A→G at nucleotide 11065; G→A at nucleotide 11518; C→T at nucleotide 12049; T→C at nucleotide 10966; G→A at nucleotide 11150; G→A at nucleotide 2056; T→C at nucleotide 2445; T→C at nucleotide 2664; T→C at nucleotide 10071; T→C at nucleotide 10321; T→C at nucleotide 12519; Δ 7 amino acids at nucleotide 15642; G→A at nucleotide 5521; G→A at nucleotide 12345; T→C substitution at position 710; T→C substitution at position 1738; T→C substitution at position 3308; G→A substitution at position 8009; G→A substitution at position 14985; T→C substitution at position 15572; G→A substitution at position 9949; T→C substitution at position 10563; G→A substitution at position 6264; A insertion at position 12418; T→C substitution at position 1967; T→A substitution at position 2299; and G→A at nucleotide 3054.

Another aspect of the invention is a method to aid in detecting the presence of tumor cells in a patient. The presence of a single basepair mutation is detected in a mitochondrial genome of a cell sample of a patient. The mutation is found in a tumor of the patient but not in normal tissue of the patient. The tumor is not a colorectal tumor. The patient is identified as having a tumor if one or more single basepair mutations are determined in the mitochondrial genome of the cell sample of the patient.

Yet another embodiment of the invention is provided by another method to aid in detecting the presence of tumor cells in a patient. The presence of a mutation is determined in a D-loop of a mitochondrial genome of a cell sample of a patient. The mutation is found in a tumor of the patient but not in normal tissue of the patient. The patient is identified as having a tumor if one or more single basepair mutations are determined in the mitochondrial genome of the cell sample of the patient.

According to still another aspect of the invention a method is provided to aid in detecting the presence of tumor cells in a patient. The presence of a single basepair mutation is determined in a mitochondrial genome of a cell sample of a patient. The mutation is found in a cancer of the patient but not in normal tissue of the patient. The cancer is selected from the group of cancers consisting of: lung, head and neck, bladder, brain, breast, lymphoma, leukaemia, skin, prostate, stomach, pancreas, liver, ovarian, uterine, testicular, and bone. The patient is identified as having a tumor if one or more single basepair mutations are determined in the mitochondrial genome of the cell sample of the patient.

According to still another aspect of the invention a method is provided to aid in detecting the presence of tumor cells in a patient. The presence of a single basepair mutation is determined in a mitochondrial genome of a cell sample of a patient. The mutation is found in a tumor of the patient but not in normal tissue of the patient. The cancer is selected from the group of cancers consisting of: lung, head and neck, and bladder. The patient is identified as having a tumor if one or more single basepair mutations are determined in the mitochondrial genome of the cell sample of the patient.

Another embodiment of the invention provides a method to aid in detecting the presence of tumor cells in a patient. The presence of a mutation in a mitochondrial genome of a cell sample of a patient is determined. The mutation is selected from the group consisting of: T→C at nucleotide 114; ΔC at nucleotide 302; C→A at nucleotide 386; insert T at nucleotide 16189; A→C at nucleotide 16265; A→T at nucleotide 16532; C→T at nucleotide 150; T→C at nucleotide 195; ΔC at nucleotide 302; C→A at nucleotide 16183; C→T at nucleotide 16187; T→C at nucleotide 16519; G→A at nucleotide 16380; G→A at nucleotide 75; insert C at nucleotide 302; insert CG at nucleotide 514; T→C at nucleotide 16172; C→T at nucleotide 16292; A→G at nucleotide 16300; A→G at nucleotide 10792; C→T at nucleotide 10793; C→T at nucleotide 10822; A→G at nucleotide 10978; A→G at nucleotide 11065; G→A at nucleotide 11518; C→T at nucleotide 12049; T→C at nucleotide 10966; G→A at nucleotide 11150; G→A at nucleotide 2056; T→C at nucleotide 2445; T→C at nucleotide 2664; T→C at nucleotide 10071; T→C at nucleotide 10321; T→C at nucleotide 12519; Δ 7 amino acids at nucleotide 15642; G→A at nucleotide 5521; G→A at nucleotide 12345; T→C substitution at position 710; T→C substitution at position 1738; T→C substitution at position 3308; G→A substitution at position 8009; G→A substitution at position 14985; T→C substitution at position 15572; G→A substitution at position 9949; T→C substitution at position 10563; G→A substitution at position 6264; A insertion at position 12418; T→C substitution at position 1967; T→A substitution at position 2299; and G→A at nucleotide 3054. The patient is identified as having a tumor if one or more mutations are determined in the mitochondrial genome of the cell sample of the patient.

These and other embodiments provide the art with non-invasive tools for monitoring exposure to and the effects of environmental pollutants on the human body as well as early detection methods for cancer and metastasis.

BRIEF DESCRIPTION OF THE DRAWINGS

FIG. 2. Sequence detection of mutated mtDNAs in samples from tumors and bodily fluids.

%, FIG. 4B), while mutant mtDNA at 16380 np (FIG. 4B) represented over 50% of the plaques (52.3%, 460/880; 19-fold) amplified from mtDNA.

Figure 5:
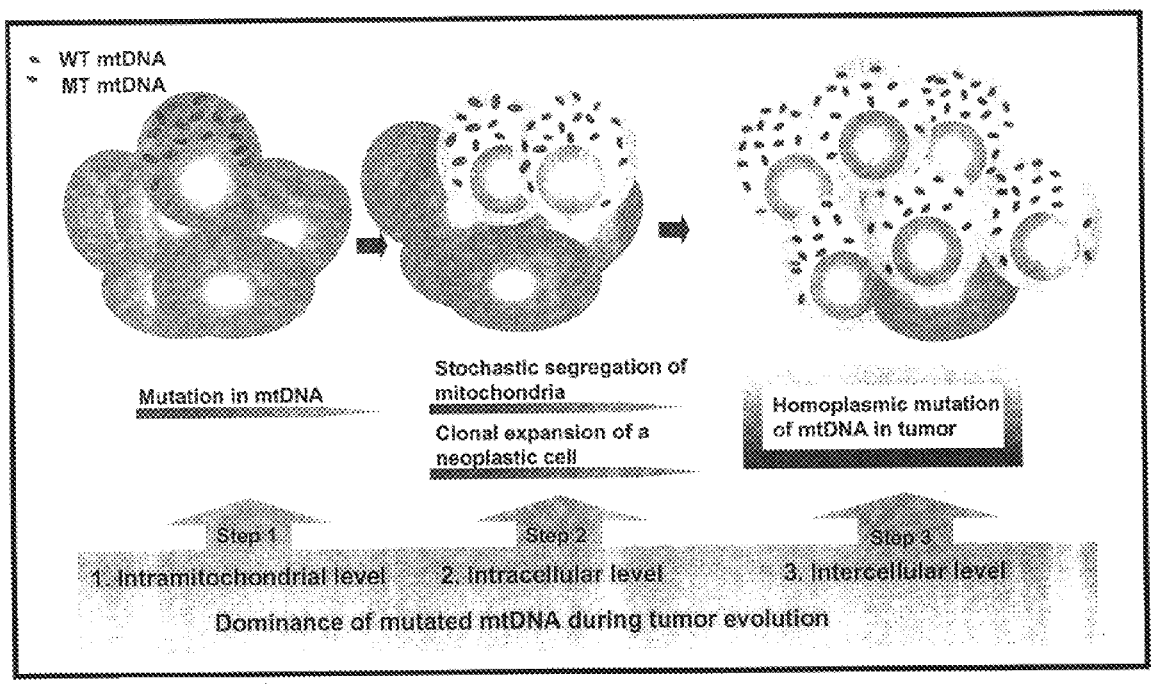

FIG. 5. Pseudoclonal selection of mtDNA. A mitochondrial genome gains some replicative advantage due to a somatic mutation (such as in the D-loop region), leading to a dominant mitochondrial genotype (step 1). This mitochondrion can gain additional replicative advantage through nuclear influences: for example, a mutated sequence gains a higher binding affinity to nuclear-encoded mitochondrial trans-acting factors (step 2). Due to its stochastic segregation together with the clonal expansion of a neoplastic cell driven by nuclear mutations, mutated mitochondria overtake the entire population of tumor cells (step 3).

BRIEF DESCRIPTION OF THE TABLES

Table 1 provides a summary of mutations in mitochondria of colorectal tumors.

Table 2 provides a summary of mutations in mitochondria of bladder, lung, head and neck tumors.

Table 3 provides a summary of new polymorphisms in mitochondria of bladder, lung, head and neck tumors.

DETAILED DESCRIPTION

It is a discovery of the present inventors that mitochondrial DNA mutations can be monitored non-invasively and sensitively and used as an indicator of environmental pollutants. It is shown below that these mutations are more prevalent in body samples than nuclear mutations, and thus are detected more sensitively. Mitochondrial mutations can be monitored over time to detect changes in the amount of exposure to pollutants. In addition, the prevalence of the mitochondrial mutation in the sample indicates whether clonal proliferation has occurred. Finally, the D-loop has been identified as a hotspot of mutations within the mitochondrial genome.

Mitochondrial mutations are determined with reference to wild-type human mitochondrial sequence. Sequence information can be found at the website having the URL address: http file type, www host server, gen.emory.edu domain name, mitomap.html directory and at SEQ ID NO: 1. However, some differences between a sample sequence and a documented wild-type sequence can be polymorphisms, not mutations. Table 3 provides a number of new polymorphisms. Other polymorphisms can be found in references 2 and 8. Polymorphisms can be distinguished from somatic mutations by comparing the sequence in the sample to the corresponding sequence in a normal body tissue of the same person. If the same variant sequence is found in the sample as in the normal body tissue it is a polymorphism. Normal tissues can be paraffin-embedded. It has been found by the present inventors that mitochondrial DNA which is paraffin-embedded remains more highly intact and amplifiable than genomic DNA. Amplifiable regions of mitochondrial DNA may be from 10 bp to about 4 kb, desirably 2 kb to 4 kb or 10 bp to about 2 kb. Other suitable sources of reference mtDNA are blood, serum, or plasma of the human being tested.

Suitable bodily fluids for testing according to the present invention include saliva, sputum, urine, and bronchoalveolar lavage (BAL). These can be collected as is known in the art. People who are prime candidates for testing and supplying such bodily fluids are those who have been episodically, periodically or chronically exposed to environmental pollutants. These include without limitation cigarette smoke, biological toxins, such as aflatoxin, cholera toxin, and botulinum toxin, radiation including UV irradiation, industrial wastes, chemicals, water-borne or air-borne pollutants, and drugs. The environmental pollutant can be known, suspected, or unidentified, as the assay depends on the effect and not on the identity of the pollutant.

The inventors have found that there are certain characteristics of the mutations which are found in mitochondrial DNA. Many mutations are found in sequences which do not encode proteins. These include the D-loop region (i.e., nucleotides 16024–526), the 16S RNA gene, and the tRNA genes. Furthermore, even where the mutations do occur in protein coding regions, they often result in silent mutations which do not affect the encoded amino acids. Other regions frequently affected include the genes for NADH dehydrogenase 4, NADH dehydrogenase 3, NADH dehydrogenase 5, and cytochrome B.

Mutation detection can be done according to any methodology which is known in the art for determining mutations. These include without limitation, nucleotide sequencing, hybridization, amplification, PCR, oligonucleotide mismatch ligation assays, primer extension assays, heteroduplex analysis, allele-specific amplification, allele-specific primer extension, SCCP, DGGE, mass spectroscopy, high pressure liquid chromatography, and combinations of these techniques.

Prevalence of a particular mutation according to the present invention can be used to monitor clonal expansion. Mutations which are present in greater than 1% of the mitochondrial DNA present in a sample have may have conferred a growth advantage on the cells harboring them. Even if no growth advantage is conferred by the mutation itself, the mutation serves as a marker for a clone which is expanding relative to the population of cells in the sample. Clonal expansion can be measured over time to monitor the growth of the clone or to monitor the efficacy of antiproliferative agents which can be considered environmental pollutants, according to the present invention.

The inventors have also found that the presence of subtle mutations in the mitochondrial genome can be used as a means to trace the presence, spread, metastasis, growth, or recurrence of a tumor in a patient. Such subtle mutations include single basepair substitutions, single basepair insertions, and single basepair deletions. Single basepair substitutions can be either transitions or transversions, although the former are more frequent. Detection of such mutations can be useful to screen for the initial appearance of a tumor as well as the recurrence of a previously identified tumor. The methods are particularly suited to monitor anticancer therapy, recurrence, metastasis, and completeness of surgical removals.

A single basepair substitution is the substitution of a single nucleotide base with a different nucleotide base at the same position, with the corresponding substitution of the complementary base on the other strand of the DNA. While any single basepair substitution is conceivable within the scope of the invention, the most frequently encountered substitutions are those which are consistent with endogenous oxidative damage, such as T to C or G to A transitions, or which are consistent with a variety of external carcinogens which cause a variety of types of mutations. The mutations can appear in protein coding or non-coding regions or in regions which encode ribosomal or transfer RNAs.

The homoplasmic or near homoplasmic property of most mutant mitochondrial genomes from tumors permits the ready detection of such mutations within a sample of mitochondrial DNA from a patient. Homoplasmic mutations are those which appear in essentially all of the copies of the mitochondrial genome within a given cell or tissue. However, heteroplasmic mutations, which are those appearing in only a fraction of the mitochondrial genomes of a cell or tissue, are also suitable for use with the invention.

Any cell sample can be tested from a patient who has cancer or is suspected of having cancer. Suitable cell samples include, but are not limited to, tissue from a growth suspected or known to be cancerous, tissue adjacent to a resection of a tumor, and tissue distant from the site of a tumor, such as lymph nodes which are suspected of bearing metastatic cells. Cells can also be obtained from bodily fluids or secretions, e.g., blood, urine, sputum, saliva, or feces, which may contain cancerous cells or metastatic cells. Cell samples can also be collected from other bodily secretions and tissues as is known in the art. A cell sample can be collected from suspected or known cancerous tissue or from bodily fluids or secretions harboring cancer cells as well as from suspected or known normal tissue or bodily fluids or secretions harboring normal cells.

In order to detect mutations of the mitochondrial genome from a cell sample of a patient, mitochondrial DNA can be isolated from the cell sample using any method known in the art. One way of identifying subtle mutations involves sequencing the mitochondrial DNA. This can be done according to any method known in the art. For example, isolated mitochondrial DNA can be cleaved using endonucleases into overlapping fragments of appropriate size for sequencing, e.g., about 1–3 kilobases in length, followed by polymerase chain reaction (PCR) amplification and sequencing of the fragments. Examples of DNA sequencing methods are found in Brumley, R. L. Jr., and Smith, L. M., 1991, Rapid DNA sequencing by horizontal ultrathin gel electrophoresis, *Nucleic Acids Res.* 19:4121–4126 and Luckey, J. A., Drossman, H., Kostihka, T.; and Smith, L. M., 1993, High-speed DNA sequencing by capillary gel electrophoresis, *Methods Enzymol.* 218:154–172. Amplification methods such as PCR can be applied to samples as small as a single cell and still yield sufficient DNA for complete sequence analysis. The combined use of PCR and sequencing of mitochondrial DNA is described in Hopgood, R., Sullivan, K. M., and Gill, P., 1992, Strategies for automated sequencing of human mitochondrial DNA directly from PCR products, *Biotechniques* 13:82–92 and Tanaka, M., Hayakawa, M., and Ozawa, T., 1996, Automated sequencing of mitochondrial DNA, *Methods Enzymol.* 264:407–21.

Mutations can first be identified by comparison to sequences present in public databases for human mitochondrial DNA, e.g., at the website having the URL address: http file type, www host server, gen.emory.edu domain name, mitomap.html directory and at SEQ ID NO: 1. Any single basepair substitution identified in the sample DNA compared to a normal sequence from a database can be confirmed as being a somatic mutation as opposed to a polymorphic variant by comparing the sample mitochondrial DNA or sequences obtained from it to control cell mitochondrial DNA from the same individual or sequences obtained from it. Control cells are isolated from other apparently normal tissues, i.e., tissues which are phenotypically normal and devoid of any visible, histological, or immunological characteristics of cancer tissue. A difference between the sample and the control identifies a somatic mutation which is associated with the tumor.

An alternative to serially sequencing the entire mitochondrial genome in order to identify a single basepair substitution is to use hybridization of the mitochondrial DNA to an array of oligonucleotides. Hybridization techniques are available in the art which can rapidly identify mutations by comparing the hybridization of the sample to matched and mismatched sequences which are based on the human mitochondrial genome. Such an array can be as simple as two oligonucleotide probes, one of whose sequence matches the wild-type or mutant region containing the single base substitution (matched probe) and another whose sequence includes a single mismatched base (mismatch control probe). If the sample DNA hybridizes to the matched probe but not the mismatched probe, it is identified as having the same sequence as the matched probe. Larger arrays containing thousands of such matched/mismatched pairs of probes on a glass slide or microchip ("microarrays" or "gene chips") are available which are capable of sequencing the entire mitochondrial genome very quickly. Such arrays are commercially available. Review articles describing the use of microarrays in genome and DNA sequence analysis and links to their commercial suppliers are available at the website having a URL address at the www host server, gen-chips domain name.

The invention can be used to screen patients suspected of having cancer for the presence of tumor cells. A cell sample is first obtained from a suspected tumor of the patient, or is obtained from another source such as blood or lymph tissue, for example, if metastasis is suspected. The cell sample is tested to determine the presence of a single basepair mutation in mitochondrial DNA from the cell sample using the techniques outlined above. Optionally, a cell sample from normal, non-cancerous cells or tissue of the patient is also obtained and is tested for the presence or absence of a single basepair mutation in mitochondrial DNA. If a single basepair mutation is determined which is not present in a cell sample from normal tissue of the patient, then the mutation is a somatic mutation and the presence of tumor cells in the patient is indicated. If one or more single basepair mutations are determined in the mitochondrial genome of the cell sample of the patient, then the patient is identified as having a tumor. As in any diagnostic technique for cancer, to confirm or extend the diagnosis, further diagnostic techniques may be warranted. For example, conventional histological examination of a biopsy specimen can be performed to detect the presence of tumor cells, or analysis of a tumor-specific antigen in a blood or tissue sample can be performed.

The method outlined above can be practiced either in the situation where the somatic mutation is previously known or previously unknown. The method can be practiced even in the absence of prior knowledge about any particular somatic mutation. The method can also be carried out subsequent to the discovery of a somatic mutation in a mitochondrial genome of a cell of the patient or of another patient. In this case, a previous association of the somatic mutation with the presence of a tumor in the patient or in another patient strongly indicates the presence of tumor cells in the patient. It may also indicate the recurrence of a tumor or the incomplete prior removal of cancerous tissue from the patient.

The effectiveness of therapy can be evaluated when a tumor has already been identified and found to contain a single basepair substitution in the mitochondrial genome. Once a single basepair mutation has been identified in the mitochondrial DNA of a tumor of the patient, further tumor cells can be detected in tissue surrounding a resection or at other sites, if metastasis has occurred. Using the methods outlined above, the recurrence of the tumor or its incomplete removal can be assessed. Similarly, if a tumor has been treated using a non-surgical method such as chemotherapy or radiation, then the success of the therapy can be evaluated at later times by repeating the analysis. The step for determining the presence of a single basepair mutation in a mitochondrial genome of a cell sample of a patient can be performed 1, 2, 3, 4, 5, 6, 8, 10, or more times in order to monitor the development or regression of a tumor or to monitor the progress or lack of progress of therapy undertaken to eliminate the tumor.

Upon repeated analyses, the step for determining the presence of a single basepair mutation is simplified, because only a well defined and limited region of the genome need be sequenced. Using the hybridization method, for example, it is possible to evaluate the presence of the mutation with only a single matched/mismatched pair of oligonucleotide probes in the array. In the event that a mixture of genotypes is observed, it is possible to obtain quantitative information about the relative amount of each mitochondrial genotype using techniques known to the art, e.g., hybridization. Quantitative analysis can reveal changes in the relative proportion of tumor to normal cells in a tissue over time or in response to therapy.

The following examples are provided to demonstrate certain aspects of the invention but they do not define the scope of the invention.

EXAMPLE 1

This example demonstrates detection of mt mutations in tissue samples.

Figure 1:
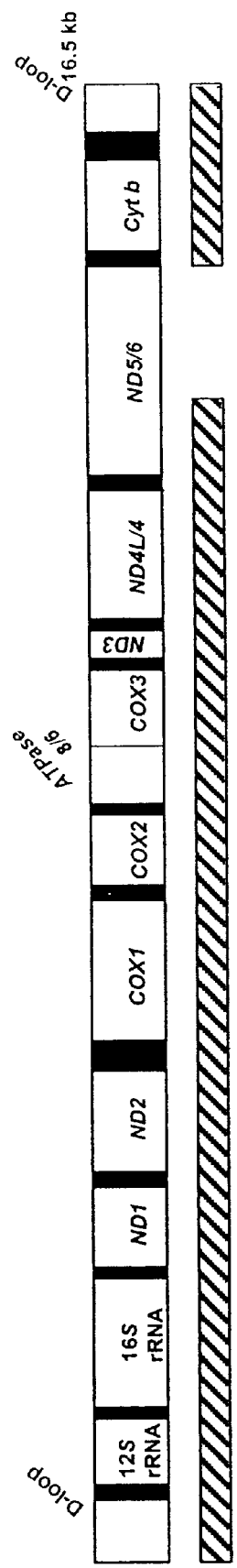
FIG. 1. Schematic representation of a linearized mt genome. Hatched bars indicate the regions sequenced in this study and solid bars indicate the positions of tRNAs (transfer RNAs). rRNA=ribosomal RNA, ND=NADH dehydrogenase, COX=cytochrome c oxidase, Cyt b=cytochrome b, ATPase=ATP synthase.

To determine whether mt mutations could be identified in cancer other than colorectal cancer, we studied primary bladder (n=14), head and neck (n=13), and lung (n=14) tumors (5). Eighty percent of the mt genome of all the primary tumor samples was PCR-amplified (6) and sequenced manually (FIG. 1). Tumor mtDNA was compared to mtDNA from paired blood samples in all cases, and mtDNA from corresponding normal tissue when available (7). Of the 292 sequence variants detected, 196 were previously recorded polymorphisms (2, 8), while 57 were novel polymorphisms (Table 3). The remaining 39 variants were acquired (somatic) mutations identified in 64% (9/14) of the bladder cancer, 46% (6/13) of the head and neck cancer, and 43% (6/14) of the lung cancer patients (Table 2). Most of these mutations were T-to-C and G-to-A base transitions, indicating possible exposure to ROS-derived mutagens (9). Similar to the previous observation by Polyak et al. (Table 1; 4), the majority of the somatic mutations identified here were also homoplasmic in nature. In addition, several of the bladder and head and neck cancers studied here (Table 2) had multiple mutations implying possible accumulation of mtDNA damage.

In the bladder tumors, mutation hot spots were primarily in the NADH dehydrogenase subunit 4 (ND4) gene (35%), and in the displacement-loop (D-loop) region (30%). The D-loop region is a critical site for both replication and expression of the mt genome since it contains the leading-strand origin of replication and the major promoters for transcription (10). Many (73%) of the mutations identified within protein-coding regions were silent, except for a (Val→Ala) substitution in the NADH dehydrogenase subunit 3 (ND3) and a 7-amino-acid deletion in cytochrome b (Cyt b). The D-loop region was also commonly mutated in head and neck cancer (67%). Two of the head and neck tumors (22%) contained mutations in the ND4 gene at nucleotide pairs (nps) 10822 and 11150, resulting in amino acid substitutions of Thr→Met and Ala→Thr, respectively. A similar tendency was observed in lung cancers, demonstrating a high concentration of mutations in the D-loop region (70%).

EXAMPLE 2

This example demonstrates detection of mt mutations in bodily fluids.

Figure 2A:
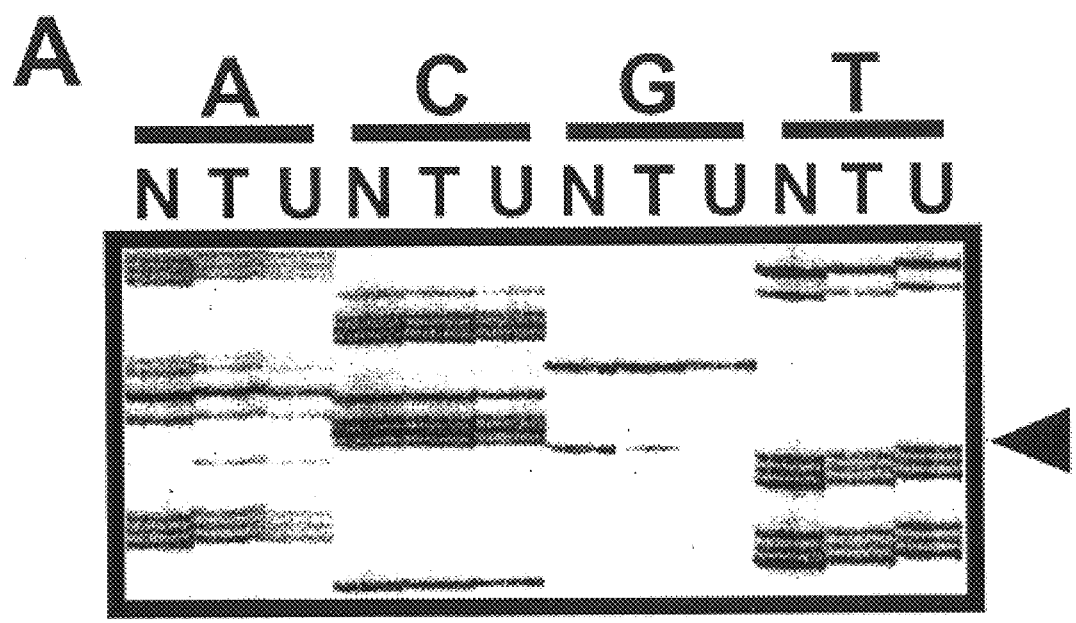
(FIG. 2A) The mt mutation was analyzed by direct sequencing of the tumor (T), normal (N), and corresponding urine (U) DNAs of bladder cancer patient #799. The arrow indicates a single nucleotide change (G(A) at 2056 np in the 16S rRNA gene.
Figure 2B:
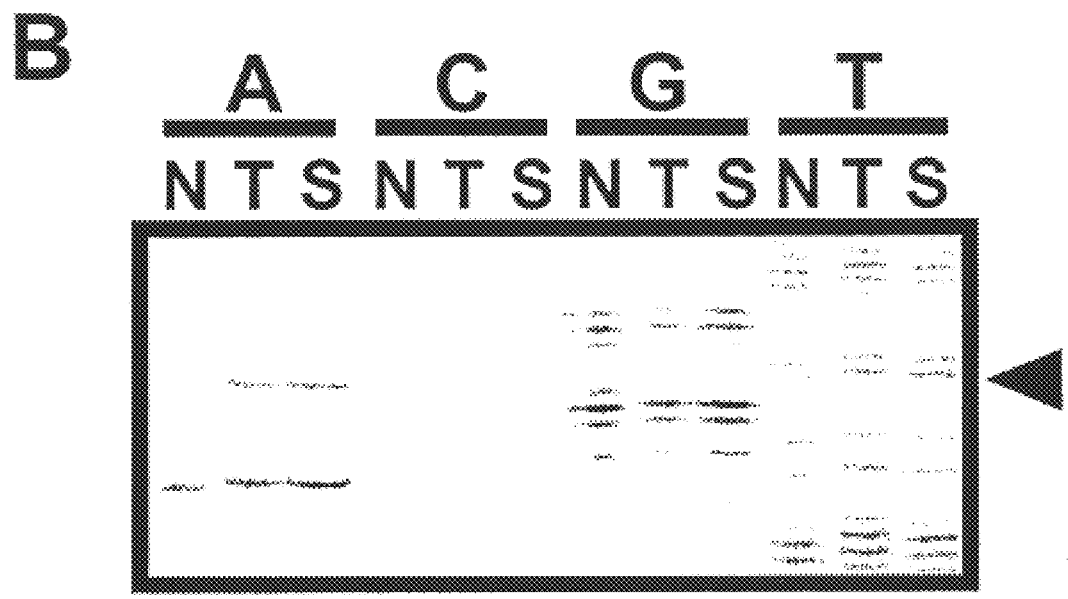
(FIG. 2B and FIG. 2C) Examples of somatic mutations in head and neck cancers. Both mutations at 16172 np (B) and 10822 np (C) were detected from saliva (S) samples from patients #1680 and #1708, respectively.
Figure 2C:
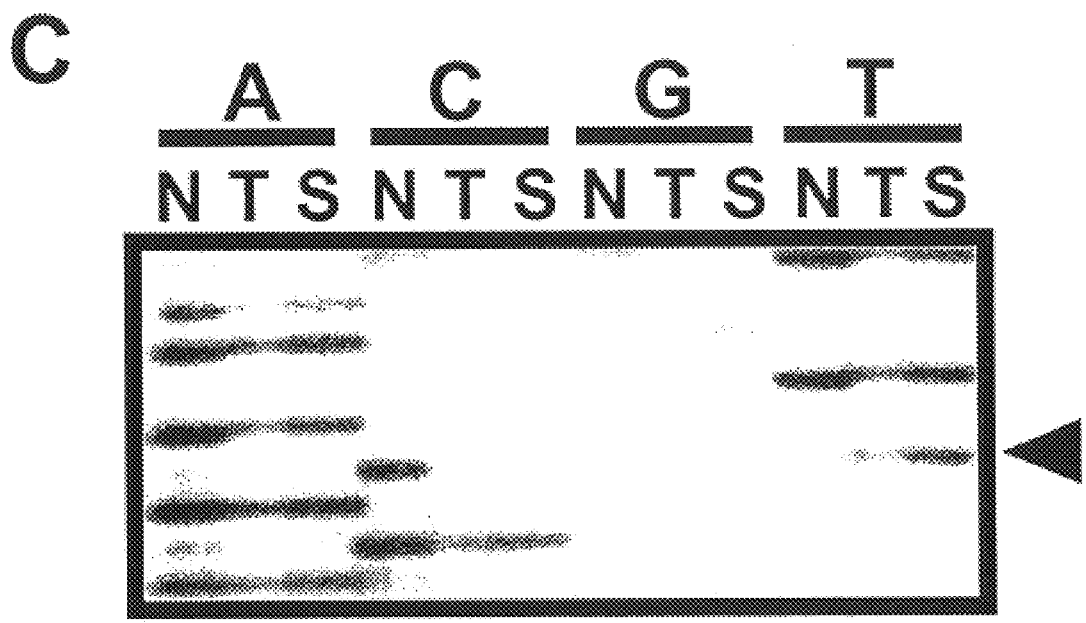
Figure 2D:
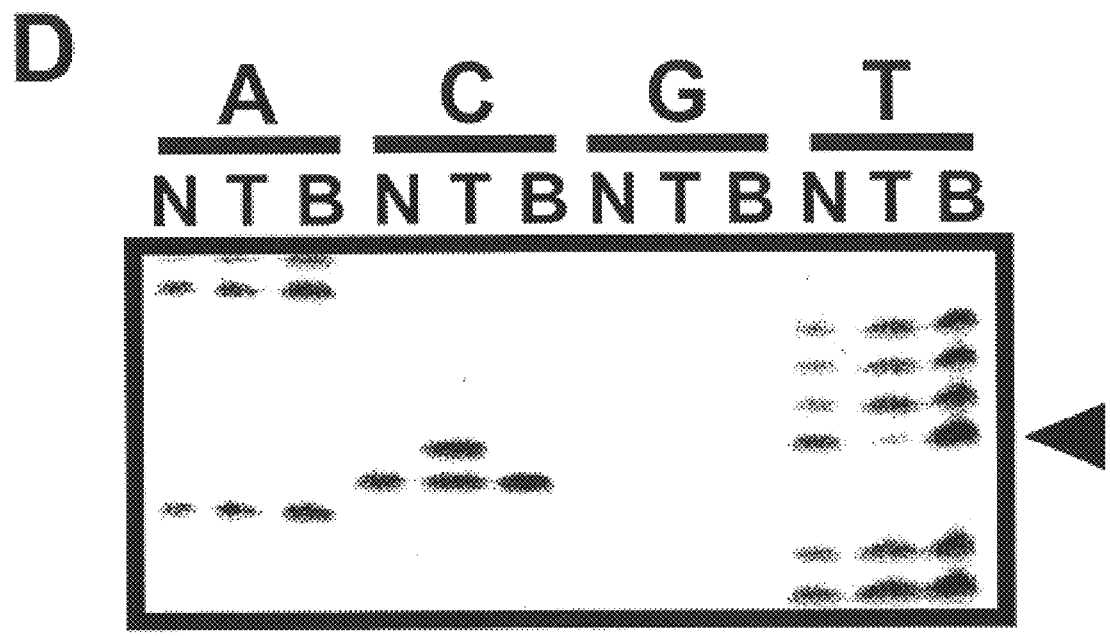
(FIG. 2D) Mutated mtDNA at 2664 np was not detected by sequence analysis in the paired BAL fluid (B), obtained from lung cancer patient #898.
Figure 3:
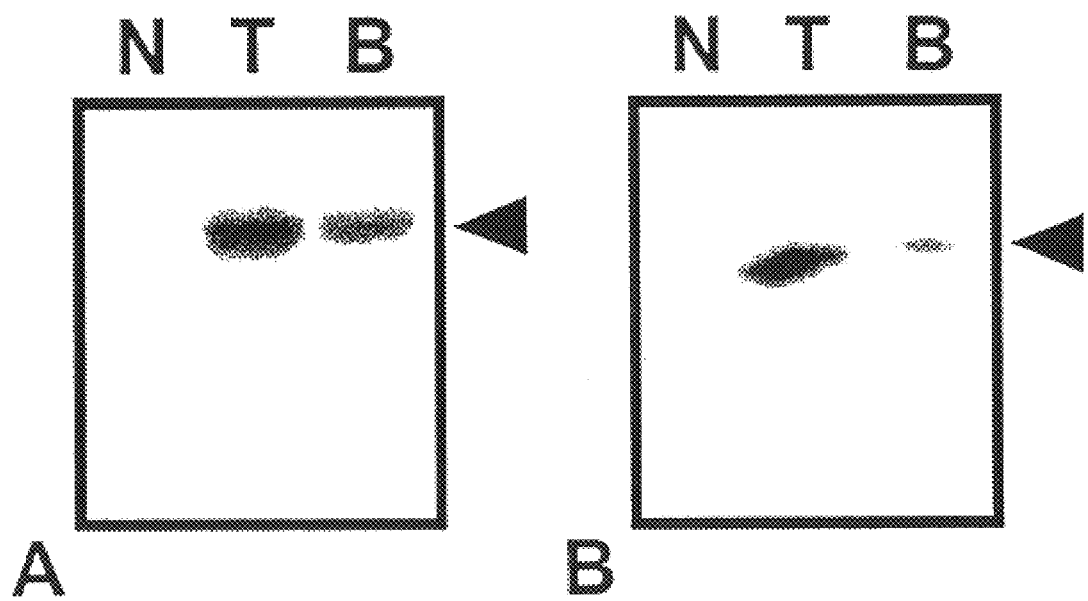
FIG. 3. Oligonucleotide-mismatch ligation assay (22) to detect mtDNA mutations in BAL. The arrows identify mutated mt sequences at 12345 np within tRNA (FIG. 3A) and at 2664 np (FIG. 3B) within 16S rRNA in the tumor DNA. More dilute signals are seen in the corresponding BAL (B) samples with no detectable signal from the paired normal (N) tissue.

We hypothesized that the homoplasmic nature of these mutations would make them readily detectable in paired bodily fluids. To test this, we extracted and directly amplified mtDNA from urine samples from patients diagnosed with bladder cancer. All three corresponding urine samples available in this study contained the mutant mtDNA derived from tumor tissues. For example, the mtDNA from a urine sample of bladder cancer patient #799 showed the same nucleotide transition (G→A) as seen in the tumor (FIG. 2A). In all cases, the urine sample contained a relatively pure population of tumor-derived mtDNA, comparable to that of the micro-dissected tumor sample. Consistent with this observation, saliva samples obtained from head and neck cancer patients contained no detectable wild-type (WT) signals (FIGS. 2B, and 2C). By sequence analysis alone, we were able to detect mtDNA mutations in 67% (6/9) of saliva samples from head and neck cancer patients. In lung cancer cases, we were initially unable to identify mutant bands from paired bronchoalveolar lavage (BAL) fluids because of the significant dilution of neoplastic cells in BAL fluid (11), (FIG. 2D). We, thus, applied a more sensitive oligonucleotide-mismatch ligation assay to detect mutated mtDNA. As shown in FIGS. 3A and 3B, both lung cancer mutations (arrows) were confirmed in tumor mtDNA with more dilute signals in the corresponding BAL samples, and no signal in the corresponding normal tissues. Again, we detected the majority of mtDNA mutations (8/10) in BAL fluids with the exception of two cases where the ligation assays were not feasible due to the sequence compositions (16183 and 302 nps) adjacent to the mutations.

EXAMPLE 3

This example demonstrates the enrichment of mitochondrial mutant DNA in samples relative to nuclear mutant DNA.

Figure 4:
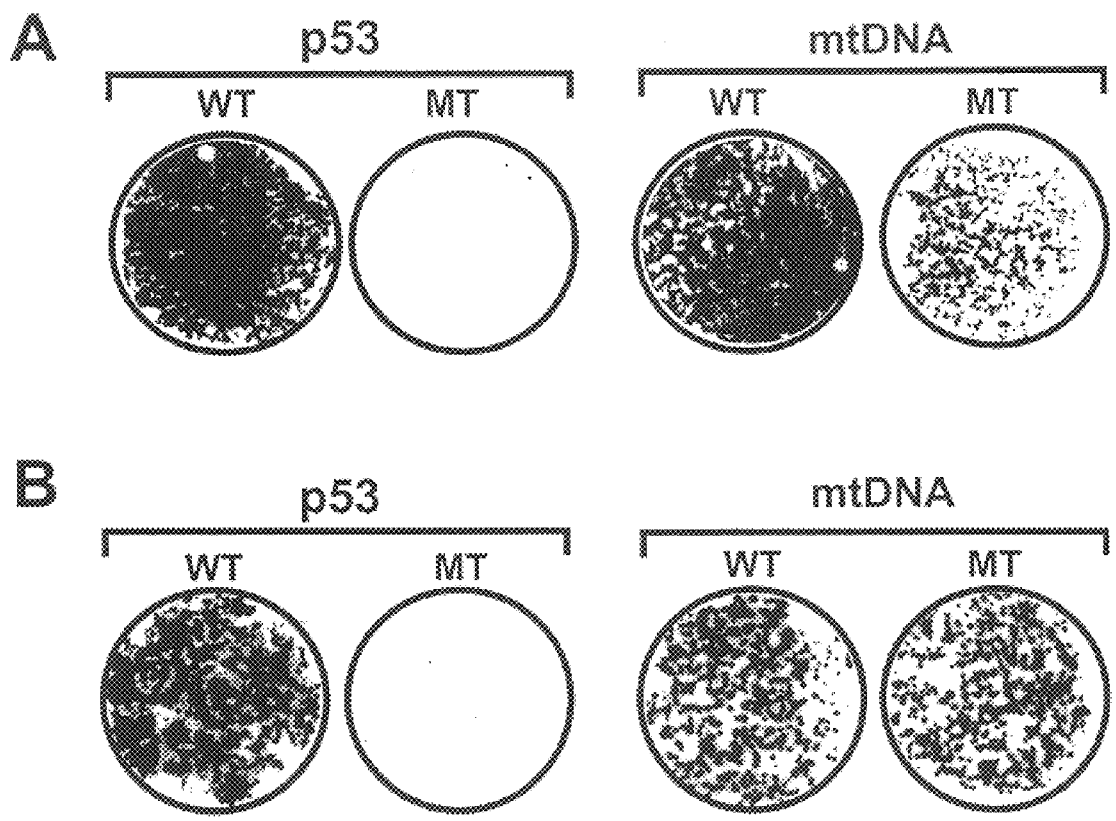
FIG. 4. Highly enriched mutated mtDNA in BAL samples from lung cancer patients. Oligonucleotide (oligo) specific hybridization detected ~2000 plaques containing WT p53 clones in the BAL from patient #1113, and only two plaques (2/2000=0.1%) with the p53 gene mutation (FIG. 4A) were found in the primary tumor. The same BAL sample demonstrated a much greater enrichment of mutated mtDNA; 445 plaques contained mtDNA mutations (FIG. 4A) at 16159 np (445/2000=22.3%; 220-fold) compared to approximately 1500 WT clones. A similar enrichment was seen in patient #1140 where oligo specific hybridization detected 12 p53 mutant plaques among 437 WT clones (2.7

To quantitate this neoplastic DNA enrichment, we compared the abundance of mt gene mutations to that of nuclear-encoded p53 mutations in bodily fluids using a quantitative plaque assay. Nuclear and mt fragments that contained a mutated sequence were PCR-amplified and cloned for plaque hybridization (12). Two BAL samples from lung cancer patients were chosen for analysis because they had mutations in both the mt and nuclear genomes. For p53 mutations, the percentages of neoplastic cells among normal cells for patients #1113 and #1140 were 0.1 and 3.0 %, respectively. Remarkably, the abundance of the corresponding mutated mtDNA (MT) was 22% and 52% when compared to the wild-type (WT) mt sequence (FIG. 4). This enrichment of mtDNA is presumably due to the homoplasmic nature of these mutations and the high copy number of mt genomes in cancer cells. Enrichment was further suggested by our observations in head and neck paraffin samples where we were able to PCR-amplify 2–3 kb fragments of mtDNA, whereas we were unable to amplify nuclear p53 gene fragments of over 300 bp.

A role for mitochondria in tumorigenesis was implicated when tumor cells were found to have an impaired respiratory system and high glycolytic activity (13,14). Recent findings elucidating the role of mitochondria in apoptosis (15) and the high incidence of mtDNA mutations in colon cancer (4) further support the original hypothesis of mitochondrial participation in the initiation and progression of cancer. Although further investigation is needed to define the functional significance of mt mutations, our data clearly show that those mutations are frequent and present at high levels in all of the tumor types examined.

The homoplasmic nature of the mutated mitochondria remains puzzling. It is estimated that each cell contains several hundred-to-thousands of mitochondria and that each mitochondrion contains 1–10 genomes (16). Conceivably, certain mutated mtDNAs may gain a significant replicative advantage. For example, mutations in the D-loop regulatory region might alter the rate of DNA replication by modifying the binding affinity of important trans-acting factors. Mitochondria that undergo the most rapid replication are likely to acquire more DNA damage, leading to an accumulation of mutational events. Although the mechanism may vary for other mutations (such as silent mutations in the ND4 gene), the accumulation of a particular mtDNA mutation may become more apparent during neoplastic transformation. Even subtle mtDNA mutations may also gain significant replicative advantage, perhaps through interactions with important nuclear factors. Homoplasmic transformation of mtDNA was observed in small populations of cells in other non-neoplastic, but diseased tissues (17), sometimes associated with aging (18). We hypothesize that, in contrast to classic clonal expansion, the process may occur as "pseudoclonal" selection where stochastic segregation of mitochondria (16) together with neoplastic clonal expansion driven by nuclear mutations lead to a homogeneous population of a previously "altered" mitochondrion (FIG. 5).

The large number of mt polymorphisms identified here and elsewhere (2) likely reflects the high mutation rate of mtDNA, which is thought to be caused mainly by high levels of ROS (19). In agreement with this, our data imply that constitutive hypervariable areas such as the D-loop region represent somatic mutational hot spots. As further mutations are tabulated in primary tumors, DNA-chip technology can be harnessed to develop high-throughput analyses with sufficient sensitivity (20, 21). Due to its high copy number, mtDNA may provide a distinct advantage over other nuclear genome based methods for cancer and environmental pollutant detection.

Literature Cited

1. R. N. Lightowlers, P. F. Chinnery, D. M. Turnbull, N. Howell, Trends Genet 13, 450 (1997).
2. MITOMAP: A Human Mitochondrial Genome Database. Center for Molecular Medicine, Emory University, Atlanta, Ga., USA. URL address: http file type, www host server, gen.emory.edu domain name, mitomap.html directory.
3. D. L. Croteau and V. A. Bohr, J. Biol. Chem. 272, 25409 (1997).
4. K. Polyak et al., *Nature Genet.* 20, 291 (1998).
5. Paired normal and tumor specimens along with blood and bodily fluids were collected following surgical resections with prior consent from patients in The Johns Hopkins University Hospital. Tumor specimens were frozen and micro-dissected on a cryostat so that the tumor samples contained greater than 70% neoplastic cells. DNA from tumor sections was digested with 1% SDS/Proteinase K, extracted by phenol-chloroform, and ethanol precipitated. Control DNA from peripheral lymphocytes, matched normal tissues, from urine, saliva, and BAL fluid were processed in the same manner as described in (11).
6. Mitochondrial DNAs were amplified using overlapping primers (4) in PCR buffer containing 6% DMSO. Approximately 5–20 ng of genomic DNA was subjected to the step-down PCR protocol: 94° C. 30 sec, 64° C. 1 min, 70° C. 3 min, 3 cycles, 94° C. 30 sec, 61° C. 1 min, 70° C. 3 min, 3 cycles 94° C. 30 sec, 58° C. 1 min, 70° C. 3.5 min 15 cycles, 94° C. 30 sec, 57° C. 1 min, 70° C. 3.5 min, 15 cycles, and a final extension at 70° C. for 5 min. PCR products were gel-purified using a Qiagen gel extraction kit (Qiagen) and sequence reactions were performed with Thermosequenase (Perkin-Elmer) using the cycle conditions (95° C. 30 sec, 52° C. 1 min, and 70° C. 1 min for 25 cycles).
7. Corresponding normal tissues from 4 patients (#874, #915, #1684, and #1678) were available and DNA was extracted from paraffin samples as described previously (9).
8. R. M. Andrew et al., Nature Genet. 23 147, (1999)
9. J. Cadet, M. Berger, T. Douki, J. L. Ravanat, Rev. Physiol. Biochem. Pharmacol. 131, 1 (1997).
8. J. W. Taanman, Biochimica. et. Biophysica. Acta. 1410, 103 (1999).
9. S. A. Ahrendt et al., J. Natl. Cancer Inst. 91, 332 (1999).
10. Subcloning of PCR fragments into phage vector was performed according to the manufacturer's instructions (Stratagene). Titered plaques were plated and subjected to hybridization using tetramethylammonium chloride (TMAC) as a solvent. Positive signals were confirmed by secondary screenings. Oligonucleotides (Oligos) used for this assay were as follows; for patient #1113, p53 and mtDNA sequence alterations were detected using oligos containing either WT-(p53: 5'-GTATTTGGATGTCAGAAACACTT-3' (SEQ ID NO: 2)/mtDNA: 5'-ACTTCAGGGTCATAAAGCC-3'(SEQ ID NO: 3)) or MT (p53: 5'-GTATTTGGATGTCAGAAACACTT-3'(SEQ ID NO: 4)/mtDNA:5'-ACTTCAGGGCCATAAAGCC-3'(SEQ ID NO: 5)) sequences, respectively. For patient #1140, oligos 5'-ACCCGCGTCCGCGCCATGGCC-3'(SEQ ID NO: 6) and 5'-ACCCGCGTCCTCGCCATGGCC-3'(SEQ ID NO: 7) were used to detect WT and MT sequences, respectively.
11. Warburg, Science 123, 309 (1956).
12. J. W. Shay and H. Werbin, Mut. Res. 186, 149 (1987).
13. D. R. Green and J. C. Reed, Science 281, 1309 (1999).
14. D. C. Wallace, Annu. Rev. Biochem. 61, 1175 (1992).
15. D. C. Wallace, Proc. Natl. Acad. Sci. USA 91, 8746 (1994).
16. K. Khrapko et al., N.A.R. 27, 2434 (1999).
17. C. Richter, J. W. Park, B. N. Ames, Proc. Natl. Acad. Sci. U S A 17, 6465 (1988).
18. M. Chee et al, *Science* 274, 610 (1996).
19. S. A. Ahrendt et al., Proc. Natl. Acad. Sci. USA 96, 7382 (1999).
20. Fragments containing mutations were PCR-amplified and then ethanol precipitated. For each mutation, discriminating oligonucleotides that contained the mutated base at the 3' end were designed (TAACCATA-3' (SEQ ID NO: 8) for patient #915 and TCTCTTACC-3' (SEQ ID NO: 9) for patient #898). Immediately adjacent [$^{32}$P] end-labeled 3' sequences (5'-CACACTACTA-3' (SEQ ID NO: 10) for patient #915 and 5'-TTTAACCAG-3' (SEQ ID NO: 11) for patient #898) were used as substrate together with discriminating oligonucleotides for the ligation reaction. After a denaturing step of 95° C. for 5', the reactions were incubated for 1 hr at 37° in the presence of T4 DNA ligase (Life Technologies), in a buffer containing 50 mM Tris-Cl, 10 mM MgCl$_2$, 150 mM NaCl, 1 mM Spermidine, 1 mM ATP, 5 mM DTT, and analyzed on denatured 12% polyacrylamide gels. [Jen et al., Cancer Res. 54, 5523 (1994)].

TABLE 1

Summary of mtDNA mutations

| Tumor* | Position | DNA | Protein | Gene |
|---|---|---|---|---|
| V478 | 710 | T→C | — | 12S rRNA |
| " | 1738 | T→C | — | 16S rRNA |
| " | 3308 | T→C | M1T | ND1 |
| V429 | 8009 | G→A | V142M | COX subunit II |
| " | 14985 | G→A | R80H | CYT b |
| " | 15572 | T→C | F276L | CYT b |
| V441 | 9949 | G→A | V248I | COX subunit III |
| V456 | 10563 | T→C | C32R | ND4L |
| V425 | 6264 | G→A | G121trun | COX subunit I |
| " | 12418 | insA | K28frameshift | ND5 |
| V451 | 1967 | T→C | — | 16S rRNA |
| V410 | 2299 | T→A | — | 16S rRNA |

*All the mutations were homoplasmic except V451 T11967C and V410 T2299A, which were present in ~50% of the mitochondrial DNA molecules.

TABLE 2

Summary of mitochondrial mutations in primary tumors.

| Patient # | Location | Sequence | Protein | Gene |
|---|---|---|---|---|
| Bladder Cancer | | (9/14, 57%) | | |
| 1124 | 114 | T→C | N/C | D-loop |
| 580 | 302 | Del C | N/C | D-loop |
| 580 | 386 | C→A | N/C | D-loop |
| 799 | 2056 | G→A | N/C | 16SrRNA |
| 716 | 2445 | T→C | N/C | 16SrRNA |
| 1127 | 3054 | G→A | N/C | 16SrRNA |
| 884 | 10071 | T→C | L-L | ND3 |
| 884 | 10321 | T→C | V-A | ND3 |
| 884 | 10792 | A→G | L-L | ND4 |
| 884 | 10793 | C→T | L-L | ND4 |
| 899 | 10822 | C→T | H-H | ND4 |
| 716 | 10978 | A→G | L-L | ND4 |
| 870 | 11065 | A→G | L-L | ND4 |
| 870 | 11518 | G→A | L-L | ND4 |
| 884 | 12049 | C→T | F-F | ND4 |
| 874 | 12519 | T→C | V-V | ND5 |
| 580 | 15642 | Del | 7aa | Cyt b |
| 899 | 16189 | Ins T | N/A | D-loop |
| 1124 | 16265 | A→C | N/A | D-loop |
| 1127 | 16532 | A→T | N/A | D-loop |
| Lung Cancer | | (6/15, 40%) | | |
| 1174 | 150 | C→T | N/C | D-loop |
| 1174 | 195 | T→C | N/C | D-loop |
| 902 | 302 | Del C | N/C | D-loop |
| 898 | 2664 | T→C | N/C | 16sRNA |
| 915 | 5521 | G→A | N/C | tRNATrp |
| 915 | 12345 | G→A | N/C | tRNALeu |
| 915 | 16183 | C→A | N/C | D-loop |
| 915 | 16187 | C→T | N/C | D-loop |
| 1113 | 16519 | T→C | N/C | D-loop |
| 1140 | 16380 | G→A | N/C | D-loop |
| Head and Neck Cancer | | (6/13, 46%) | | |
| 1637 | 75 | G→A | N/C | D-loop |
| 1680 | 302 | Ins C | N/C | D-loop |
| 1565 | 514 | Ins CG | N/C | D-loop |
| 1708 | 10966 | T→C | T→T | ND 4 |
| 1678 | 11150 | G→A | A→T | ND 4 |
| 1680 | 16172 | T→C | N/C | D-loop |
| 1680 | 16292 | C→T | N/C | D-loop |
| 1680 | 16300 | A→G | N/C | D-loop |

Only D-loop region was analyzed for lung patients # 1113, #1140, and #1174

TABLE 3

New mtDNA polymorphisms (n = 57) found in this study.

| Tumor | Position | Gene | Sequence change DNA | Protein |
|---|---|---|---|---|
| B | 633 | tRNA Phe | A→G | — |
| B | 723 | 12S rRNA | A→G | — |
| B, L, HNC | 1738 | 16S rRNA | T→C | — |
| B | 1872 | 16S rRNA | T→C | — |
| L | 2308 | 16S rRNA | A→G | — |
| B, L | 2395 | 16S rRNA | Del A | — |
| HNC | 2712 | 16S rRNA | G→A | — |
| HNC | 2758 | 16S rRNA | G→A | — |
| L | 2768 | 16S rRNA | A→G | — |
| HNC | 2768 | 16S rRNA | A→C | — |
| HNC | 3148 | 16S rRNA | C→T | — |
| B, L, HNC | 3308 | ND1 | T→C | M→T |
| B | 4823 | ND2 | T→C | V→V |
| B | 4917 | ND2 | A→G | N→D |
| B | 5509 | ND2 | T→C | L→S |
| B | 5567 | tRNA Trp | T→C | — |
| B | 5580 | NCN | T→C | — |
| B | 5899 | NCN | Del C | — |
| B | 6149 | CoxI | A→G | L→L |
| B | 6150 | CoxI | G→A | V→I |
| B | 6253 | CoxI | T→C | M→T |
| B | 6261 | CoxI | G→A | A→T |
| B | 6302 | CoxI | A→G | A→A |
| B | 7966 | CoxII | C→T | F→F |
| B | 8037 | CoxII | G→A | R→H |
| B | 8248 | CoxII | A→G | M→M |
| B | 8655 | ATPase6 | C→T | I→I |
| B | 8877 | ATPase6 | T→C | F→F |
| B | 9072 | ATPase6 | A→G | S→S |
| B | 9093 | ATPase6 | A→G | T→T |
| B | 9266 | CoxIII | G→A | G→G |
| B | 9497 | CoxIII | T→C | F→F |
| L | 10321 | ND3 | T→C | V→A |
| HNC | 10403 | ND 3 | A→G | E→E |
| B, L, HNC | 10688 | ND 4L | G→A | V→V |
| B, L, HNC | 10810 | ND 4 | T→C | L→L |
| B | 11164 | ND 4 | A→G | R→R |
| L | 11257 | ND 4 | C→T | Y→Y |
| HNC | 11339 | ND 4 | T→C | L→L |
| L | 11899 | ND 4 | T→C | S→S |
| L | 12519 | ND 5 | T→C | V→V |
| B, L | 14769 | Cyt b | A→G | N→S |
| B | 14992 | Cyt b | T→C | L→L |
| L | 15139 | Cyt b | T→C | Y→Y |
| L | 15514 | Cyt b | T→C | Y→Y |
| L | 15586 | Cyt b | T→C | I→I |
| B | 15601 | Cyt b | T→C | P→P |
| L | 15670 | Cyt b | T→C | H→H |
| B | 15672 | Cyt b | T→C | M→T |
| B | 15787 | Cyt b | T→C | F→F |
| HNC | 15941 | tRNA Thr | T→C | — |
| L | 15942 | tRNA Thr | T→C | — |
| B | 16130 | D-Loop | G→A | — |
| L | 16170 | D-Loop | A→G | — |
| L | 16204 | D-Loop | G→C | — |
| L | 16211 | D-Loop | C→T | — |
| B | 16225 | D-Loop | C→T | — |

B = Bladder cancer; L = Lung cancer; HNC = Head and neck cancer; NCN = non-coding nucleotide.

What is claimed is:

1. A method to aid in detecting the presence of tumor cells in a human patient, comprising:

determining the presence of a mutation in a D-loop of a mitochondrial genome of a cell sample of a human patient, wherein the mutation is found in a tumor of the human patient but not in normal tissue of the human patient; wherein the tumor is selected from the group of tumors consisting of: lung, head and neck, bladder, prostate, and pancreas; and identifying the human patient as having a tumor if one or more single basepair mutations are determined in the mitochondrial genome of the cell sample of the human patient.

2. The method of claim 1 wherein the mutation is selected from the group consisting of: T→C at nucleotide 114; ΔC at nucleotide 302; C→A at nucleotide 386; insert T at nucleotide 16189; A→C at nucleotide 16265; A→T at nucleotide 16532; C→T at nucleotide 150; T→C at nucleotide 195; ΔC at nucleotide 302; C→A at nucleotide 16183; C→T at nucleotide 16187; T→C at nucleotide 16519; G→A at nucleotide 16380; G→A at nucleotide 75; insert C at nucleotide 302; insert C→G at nucleotide 514; T→C at nucleotide 16172; C→T at nucleotide 16292; and A→G at nucleotide 16300.

3. A method to aid in detecting the presence of tumor cells in a human patient, comprising:

determining the presence of a single basepair mutation in a mitochondrial genome of a cell sample of a human patient, wherein the mutation is found in a cancer of the human patient but not in normal tissue of the human patient, wherein the cancer is selected from the group of cancers consisting of: lung, head and neck, bladder, prostate, and pancreas; and identifying the human patient as having a tumor if one or more single basepair mutations are determined in the mitochondrial genome of the cell sample of the human patient.

4. A method to aid in detecting the presence of tumor cells in a patient, comprising:

determining the presence of a mutation in a mitochondrial genome of a cell sample of a patient, wherein the mutation is selected from the group consisting of: T→C at nucleotide 114; ΔC at nucleotide 302; C→A at nucleotide 386; insert T at nucleotide 16189; A→C at nucleotide 16265; A→T at nucleotide 16532; C→T at nucleotide 150; T→C at nucleotide 195; C→A at nucleotide 16183; C→T at nucleotide 16187; T→C at nucleotide 16519; G→A at nucleotide 16380; G→A at nucleotide 75; insert C at nucleotide 302; insert C→G at nucleotide 514; T→C at nucleotide 16172; C→T at nucleotide 16292; A→G at nucleotide 16300; A→G at nucleotide 10792; C→T at nucleotide 10793; C→T at nucleotide 10822; A→G at nucleotide 10978; A→G at nucleotide 11065; G→A at nucleotide 11518; C→T at nucleotide 12049; T→C at nucleotide 10966; G→A at nucleotide 11150; G→A at nucleotide 2056; T→C at nucleotide 2445; T→C at nucleotide 2664; T→C at nucleotide 10071; T→C at nucleotide 10321; T→C at nucleotide 12519 ; Δ 7 amino acids at nucleotide 15642; G→A at nucleotide 5521; G→A at nucleotide 12345; and G→A at nucleotide 3054; and identifying the patient as having a tumor selected from the group of tumors consisting of: lung, head and neck, bladder, breast, prostate, pancreas, and liver if one or more mutations are determined in the mitochondrial genome of the cell sample of the patient.

5. The method of claim 1, 3, or 4 wherein the cell sample is from blood.

6. The method of claim 1, 3, or 4 wherein the cell sample is from urine.

7. The method of claim 1, 3, or 4 wherein the cell sample is from sputum.

8. The method of claim 1, 3, or 4 wherein the cell sample is from saliva.

9. The method of claim 1, 3, or 4 wherein the cell sample is from feces.

10. The method of claim 1, 3, or 4 wherein the step for determining comprises amplifying mitochondrial DNA.

11. The method of claim 1, 3, or 4 wherein the step for determining comprises sequencing mitochondrial DNA.

12. The method of claim 1, 3, or 4 wherein the step for determining comprises hybridization of DNA amplified from the mitochondrial genome of the cell sample to an array of oligonucleotides which comprises matched and mismatched sequences to human mitochondrial genomic DNA.

13. The method of claim 1, 3, or 4 wherein the mutation is a substitution mutation.

14. The method of claim 1, 3, or 4 wherein the mutation is a one basepair insertion.

15. The method of claim 1, 3, or 4 wherein the mutation is a one basepair deletion.

16. The method of claim 1, 3, or 4 wherein the mutation is a transition mutation.

17. The method of claim 1, 3, or 4 wherein the mutation is a homoplasmic mutation.

18. The method of claim 4 wherein the mutation is T→C at nucleotide 114.

19. The method of claim 4 wherein the mutation is ΔC at nucleotide 302.

20. The method of claim 4 wherein the mutation is C→A at nucleotide 386.

21. The method of claim 4 wherein the mutation is insert T at nucleotide 16189.

22. The method of claim 4 wherein the mutation is A→C at nucleotide 16265.

23. The method of claim 4 wherein the mutation is A→T at nucleotide 16532.

24. The method of claim 4 wherein the mutation is C→T at nucleotide 150.

25. The method of claim 4 wherein the mutation is T→C at nucleotide 195.

26. The method of claim 4 wherein the mutation is C→A at nucleotide 16183.

27. The method of claim 4 wherein the mutation is C→T at nucleotide 16187.

28. The method of claim 4 wherein the mutation is T→C at nucleotide 16519.

29. The method of claim 4 wherein the mutation is G→A at nucleotide 16380.

30. The method of claim 4 wherein the mutation is G→A at nucleotide 75.

31. The method of claim 4 wherein the mutation is insert C at nucleotide 302.

32. The method of claim 4 wherein the mutation is insert CG at nucleotide 514.

33. The method of claim 4 wherein the mutation is T→C at nucleotide 16172.

34. The method of claim 4 wherein the mutation is C→T at nucleotide 16292.

35. The method of claim 4 wherein the mutation is A→G at nucleotide 16300.

36. The method of claim 4 wherein the mutation is A→G at nucleotide 10792.

37. The method of claim 4 wherein the mutation is C→T at nucleotide 10822.

38. The method of claim 4 wherein the mutation is C→T at nucleotide 10782.

39. The method of claim 4 wherein the mutation is A→G at nucleotide 10695.

40. The method of claim 4 wherein the mutation is A→G at nucleotide 110822.

41. The method of claim 4 wherein the mutation is G→A at nucleotide 11518.

42. The method of claim 4 wherein the mutation is C→T at nucleotide 12049.

43. The method of claim 4 wherein the mutation is T→C at nucleotide 10966.

44. The method of claim 4 wherein the mutation is G→A at nucleotide 11150.

45. The method of claim 4 wherein the mutation is G→A at nucleotide 2056.

46. The method of claim 4 wherein the mutation is T→C at nucleotide 2445.

47. The method of claim 4 wherein the mutation is T→C at nucleotide 2664.

48. The method of claim 4 wherein the mutation is T→C at nucleotide 10071.

49. The method of claim 4 wherein the mutation is T→C at nucleotide 10321.

50. The method of claim 4 wherein the mutation is T→C at nucleotide 12519.

51. The method of claim 4 wherein the mutation is Δ 7 amino acids at nucleotide 15642.

52. The method of claim 4 wherein the mutation is G→A at nucleotide 5521.

53. The method of claim 4 wherein the mutation is G→A at nucleotide 12345.

54. The method of claim 4 wherein the mutation is G→A at nucleotide 3054.

* * * * *

UNITED STATES PATENT AND TRADEMARK OFFICE
CERTIFICATE OF CORRECTION

PATENT NO. : 6,605,433 B1 Page 1 of 1
DATED : August 12, 2003
INVENTOR(S) : Fliss et al.

It is certified that error appears in the above-identified patent and that said Letters Patent is hereby corrected as shown below:

Column 31,
Line 53, "insert C→G at nucleotide 514" has been replaced with -- insert CG at nucleotide 514 --.

Column 32,
Lines 43-44, "insert C→G at nucleotide 514" has been replaced with -- insert CG at nucleotide 514 --.

Column 34,
Line 13, "10822" has been replaced with -- 10793 --.
Line 15, "10782" has been replaced with -- 10822 --.
Line 17, "10695" has been replaced with -- 10978 --.
Line 19, "110822" has been replaced with -- 11065 --.

Signed and Sealed this

Tenth Day of February, 2004

JON W. DUDAS
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 6,605,433 B1 | Page 1 of 1 |
| APPLICATION NO. | : 09/525906 | |
| DATED | : August 12, 2003 | |
| INVENTOR(S) | : Makiko Fliss et al. | |

It is certified that error appears in the above-identified patent and that said Letters Patent is hereby corrected as shown below:

Title Page, Inventors,
Please delete "Komelia" and insert --Kornelia--

Signed and Sealed this

Thirteenth Day of September, 2011

David J. Kappos
*Director of the United States Patent and Trademark Office*

SEQUENCE LISTING

<160> NUMBER OF SEQ ID NOS: 11

<210> SEQ ID NO 1
<211> LENGTH: 16568
<212> TYPE: DNA
<213> ORGANISM: Homo sapiens

<400> SEQUENCE: 1

| | | | | | |
|---|---|---|---|---|---|
| gatcacaggt | ctatcaccct | attaaccact | cacgggagct | ctccatgcat | ttggtatttt   60 |
| cgtctggggg | gtatgcacgc | gatagcattg | cgagacgctg | gagccggagc | accctatgtc  120 |
| gcagtatctg | tctttgattc | ctgcctcatc | ctattattta | tcgcacctac | gttcaatatt  180 |
| acaggcgaac | atacttacta | aagtgtgtta | attaattaat | gcttgtagga | cataataata  240 |
| acaattgaat | gtctgcacag | ccactttcca | cacagacatc | ataacaaaaa | atttccacca  300 |
| aacccccccct | ccccgcttc | tggccacagc | acttaaacac | atctctgcca | accccaaaa  360 |
| acaaagaacc | ctaacaccag | cctaaccaga | tttcaaattt | tatcttttgg | cggtatgcac  420 |
| ttttaacagt | caccccccaa | ctaacacatt | attttcccct | cccactccca | tactactaat  480 |
| ctcatcaata | caaccccgc | ccatcctacc | cagcacacac | acaccgctgc | taacccata  540 |
| ccccgaacca | accaaacccc | aaagacaccc | cccacagttt | atgtagctta | cctcctcaaa  600 |
| gcaatacact | gaaaatgttt | agacgggctc | acatcacccc | ataaacaaat | aggtttggtc  660 |
| ctagccttttc | tattagctct | tagtaagatt | acacatgcaa | gcatcccgt | tccagtgagt  720 |
| tcaccctcta | aatcaccacg | atcaaaagga | acaagcatca | agcacgcagc | aatgcagctc  780 |
| aaaacgctta | gcctagccac | accccacgg | gaaacagcag | tgattaacct | ttagcaataa  840 |
| acgaaagttt | aactaagcta | tactaacccc | agggttggtc | aatttcgtgc | cagccaccgc  900 |
| ggtcacacga | ttaacccaag | tcaatagaag | ccggcgtaaa | gagtgtttta | gatcaccccc  960 |
| tccccaataa | agctaaaact | cacctgagtt | gtaaaaaact | ccagttgaca | caaaatagac 1020 |
| tacgaaagtg | gctttaacat | atctgaacac | acaatagcta | agacccaaac | tgggattaga 1080 |
| taccccacta | tgcttagccc | taaacctcaa | cagttaaatc | aacaaaactg | ctcgccagaa 1140 |
| cactacgagc | cacagcttaa | aactcaaagg | acctggcggt | gcttcatatc | cctctagagg 1200 |
| agcctgttct | gtaatcgata | aaccccgatc | aacctcacca | cctcttgctc | agcctatata 1260 |
| ccgccatctt | cagcaaaccc | tgatgaaggc | tacaaagtaa | gcgcaagtac | ccacgtaaag 1320 |
| acgttaggtc | aaggtgtagc | ccatgaggtg | gcaagaaatg | ggctacattt | tctacccag 1380 |
| aaaactacga | tagcccttat | gaaacttaag | ggtcgaaggt | ggatttagca | gtaaactaag 1440 |
| agtagagtgc | ttagttgaac | agggccctga | agcgcgtaca | caccgcccgt | caccctcctc 1500 |
| aagtatactt | caaaggacat | ttaactaaaa | cccctacgca | tttatataga | ggagacaagt 1560 |
| cgtaacatgg | taagtgtact | ggaaagtgca | cttggacgaa | ccagagtgta | gcttaacaca 1620 |
| aagcacccaa | cttacactta | ggagatttca | acttaacttg | accgctctga | gctaaaccta 1680 |
| gccccaaacc | cactccacct | tactaccaga | caaccttagc | caaaccatt | acccaaataa 1740 |
| agtataggcg | atagaaattg | aaacctggcg | caatagatat | agtaccgcaa | gggaaagatg 1800 |
| aaaaattata | accaagcata | atatagcaag | gactaacccc | tataccttct | gcataatgaa 1860 |
| ttaactagaa | ataactttgc | aaggagagcc | aaagctaaga | cccccgaaac | cagacgagct 1920 |
| acctaagaac | agctaaaaga | gcacaccgt | ctatgtagca | aaatagtggg | aagatttata 1980 |
| ggtagaggcg | acaaacctac | cgagcctggt | gatagctggt | tgtccaagat | agaatcttag 2040 |

```
ttcaactttta aatttgccca cagaaccctc taaatcccct tgtaaattta actgttagtc    2100
caaagaggaa cagctctttg gacactagga aaaaaccttg tagagagagt aaaaaattta    2160
acacccatag taggcctaaa agcagccacc aattaagaaa gcgttcaagc tcaacaccca    2220
ctacctaaaa aatcccaaac atataactga actcctcaca cccaattgga ccaatctatc    2280
accctataga agaactaatg ttagtataag taacatgaaa acattctcct ccgcataagc    2340
ctgcgtcaga ttaaaacact gaactgacaa ttaacagccc aatatctaca atcaaccaac    2400
aagtcattat taccctcact gtcaacccaa cacaggcatg ctcataagga aaggttaaaa    2460
aaagtaaaag gaactcggca aatcttaccc cgcctgttta ccaaaaacat cacctctagc    2520
atcaccagta ttagaggcac cgcctgccca gtgacacatg tttaacggcc gcggtaccct    2580
aaccgtgcaa aggtagcata atcacttgtt ccttaaatag ggacctgtat gaatggctcc    2640
acgagggttc agctgtctct tacttttaac cagtgaaatt gacctgcccg tgaagaggcg    2700
ggcataacac agcaagacga aagaccccta tggagcttta atttattaat gcaaacagta    2760
cctaacaaac ccacaggtcc taaactacca aacctgcatt aaaaatttcg gttggggcga    2820
cctcggagca gaacccaacc tccgagcagt acatgctaag acttcaccag tcaaagcgaa    2880
ctactatact caattgatcc aataacttga ccaacgaaac aagttaccct agggataaca    2940
gcgcaatcct attctagagt ccatatcaac aatagggttt acgacctcga tgttggatca    3000
ggacatcccg atggtgcagc cgctattaaa ggttcgtttg ttcaacgatt aaagtcctac    3060
gtgatctgag ttcagaccgg agtaatccag gtcggtttct atctacttca aattcctccc    3120
tgtacgaaag gacaagagaa ataaggccta cttcacaaag cgccttcccc cgtaaatgat    3180
atcatctcaa cttagtatta tacccacacc cacccaagaa cagggtttgt taagatggca    3240
gagcccggta atcgcataaa acttaaaact ttacagtcag aggttcaatt cctcttctta    3300
acaacatacc catgccaac ctcctactcc tcattgtacc cattctaatc gcaatggcat    3360
tcctaatgct taccgaacga aaaattctag gctatataca actacgcaaa ggccccaacg    3420
ttgtaggccc ctacgggcta ctacaaccct tcgctgacgc cataaaactc ttcaccaaag    3480
agccctaaa accgccaca tctaccatca ccctctacat caccgccccg accttagctc    3540
tcaccatcgc tcttctacta tgaaccccc tccccatacc caaccccctg gtcaacctca    3600
acctaggcct cctatttatt ctagccacct ctagcctagc cgtttactca atcctctgat    3660
cagggtgagc atcaaactca aactacgccc tgatcggcgc actgcgagca gtagcccaaa    3720
caatctcata tgaagtcacc ctagccatca ttctactatc aacattacta ataagtggct    3780
cctttaacct ctccacccct atcacaacac aagaacacct ctgattactc ctgccatcat    3840
gacccttggc cataatatga tttatctcca cactagcaga gaccaaccga acccccttcg    3900
accttgccga agggggagtcc gaactagtct caggcttcaa catcgaatac gccgcaggcc    3960
ccttcgccct attcttcata gccgaataca caaacattat tataaataac ccctcacca    4020
ctacaatctt cctaggaaca acatatgacg cactctcccc tgaactctac acaacatatt    4080
ttgtcaccaa gaccctactt ctaacctccc tgttcttatg aattcgaaca gcatacccc    4140
gattccgcta cgaccaactc atacacctcc tatgaaaaaa cttcctacca ctcaccctag    4200
cattacttat atgatatgtc tccataccca ttacaatctc cagcattccc cctcaaacct    4260
aagaaatatg tctgataaaa gagttacttt gatagagtaa ataataggag cttaaacccc    4320
cttatttcta ggactatgag aatcgaaccc atccctgaga atccaaaatt ctccgtgcca    4380
```

-continued

```
cctatcacac cccatcctaa agtaaggtca gctaaataag ctatcgggcc catacccga    4440
aaatgttggt tataccette cegtactaat taatcccctg gcccaacccg tcatctactc    4500
taccatcttt gcaggcacac tcatcacagc gctaagctcg cactgatttt ttacctgagt   4560
aggcctagaa ataaacatgc tagctttat tccagttcta accaaaaaaa taaaccctcg    4620
ttccacagaa gctgccatca agtatttcct cacgcaagca accgcatcca taatccttct   4680
aatagctatc ctcttcaaca atatactctc cggacaatga accataacca atactaccaa   4740
tcaatactca tcattaataa tcataatagc tatagcaata aaactaggaa tagccccctt   4800
tcacttctga gtcccagagg ttacccaagg cacccctctg acatccggcc tgcttcttct   4860
cacatgacaa aaactagccc ccatctcaat catataccaa atctctccct cactaaacgt   4920
aagccttctc ctcactctct caatcttatc catcatagca ggcagttgag gtggattaaa   4980
ccaaacccag ctacgcaaaa tcttagcata ctcctcaatt acccacatag gatgaataat   5040
agcagttcta ccgtacaacc ctaacataac cattcttaat ttaactattt atattatcct   5100
aactactacc gcattcctac tactcaactt aaactccagc accacgaccc tactactatc   5160
tcgcacctga aacaagctaa catgactaac acccttaatt ccatccaccc tcctctccct   5220
aggaggcctg cccccgctaa ccggctttt gcccaaatgg gccattatcg aagaattcac   5280
aaaaaacaat agcctcatca tccccaccat catagccacc atcaccctcc ttaacctcta   5340
cttctaccta cgcctaatct actccacctc aatcacacta ctccccatat ctaacaacgt   5400
aaaaataaaa tgacagtttg aacatacaaa acccaccca ttcctcccca cactcatcgc   5460
ccttaccacg ctactcctac ctatctcccc ttttatacta ataatcttat agaaatttag   5520
gttaaataca gaccaagagc cttcaaagcc ctcagtaagt tgcaatactt aatttctgta   5580
acagctaagg actgcaaaac cccactctgc atcaactgaa cgcaaatcag ccactttaat   5640
taagctaagc ccttactaga ccaatgggac ttaaacccac aaaacttag ttaacagcta   5700
agcaccctaa tcaactggct tcaatctact ctcccgccg ccgggaaaaa aggcgggaga   5760
agccccggca ggtttgaagc tgcttcttcg aatttgcaat tcaatatgaa atcaccctcg   5820
gagctggtaa aaagaggcct aaccctgtc tttagattta cagtccaatg cttcactcag   5880
ccattttacc tcaccccac tgatgttcgc cgaccgttga ctattctcta caaccacaa   5940
agacattgga acactatacc tattattcgg cgcatgagct ggagtcctag gcacagctct   6000
aagcctcctt attcgagccg agctgggcca gccaggcaac cttctaggta acgaccacat   6060
ctacaacgtt atcgtcacag cccatgcatt tgtaataatc ttcttcatag taatacccat   6120
cataatcgga ggctttggca actgactagt tccectaata atcggtgccc ccgatatggc   6180
gtttccccgc ataaacaaca taagcttctg actcttacct ccctctctcc tactcctgct   6240
cgcatctgct atagtggagg ccggagcagg aacaggttga acagtctacc ctcccttagc   6300
agggaactac tcccacctg gagcctccgt agacctaacc atcttctcct tacacctagc   6360
aggtgtctcc tctatcttag gggccatcaa tttcatcaca acaattatca atataaaacc   6420
ccctgccata acccaatacc aaacgcccct cttcgtctga tccgtcctaa tcacagcagt   6480
cctacttctc ctatctctcc cagtcctagc tgctggcatc actatactac taacagaccg   6540
caacctcaac accaccttct tcgaccccgc cggaggagga gaccccattc tataccaaca   6600
cctattctga ttttcggtc accctgaagt ttatattctt atcctaccag gcttcggaat   6660
aatctcccat attgtaactt actactccgg aaaaaaagaa ccatttggat acataggtat   6720
ggtctgagct atgatatcaa ttggcttcct agggtttatc gtgtgagcac accatatatt   6780
```

```
tacagtagga atagacgtag acacacgagc atatttcacc tccgctacca taatcatcgc   6840
tatccccacc ggcgtcaaag tatttagctg actcgccaca ctccacggaa gcaatatgaa   6900
atgatctgct gcagtgctct gagccctagg attcatcttt cttttcaccg taggtggcct   6960
gactggcatt gtattagcaa actcatcact agacatcgta ctacacgaca cgtactacgt   7020
tgtagcccac ttccactatg tcctatcaat aggagctgta tttgccatca taggaggctt   7080
cattcactga tttcccctat tctcaggcta caccctagac caaacctacg ccaaaatcca   7140
tttcactatc atattcatcg gcgtaaatct aactttcttc ccacaacact ttctcggcct   7200
atccggaatg ccccgacgtt actcggacta ccccgatgca tacaccacat gaaacatcct   7260
atcatctgta ggctcattca tttctctaac agcagtaata ttaataattt tcatgatttg   7320
agaagccttc gcttcgaagc gaaaagtcct aatagtagaa gaaccctcca taaacctgga   7380
gtgactatat ggatgccccc caccctacca cacattcgaa gaacccgtat acataaaatc   7440
tagacaaaaa aggaaggaat cgaacccccc aaagctggtt tcaagccaac cccatggcct   7500
ccatgacttt ttcaaaaagg tattagaaaa accatttcat aactttgtca agttaaatt    7560 ataggctaaa tcctatatat cttaatggca catgcagcgc aagtaggtct acaagacgct   7620
acttccccta tcatagaaga gcttatcacc tttcatgatc acgccctcat aatcattttc   7680
cttatctgct tcctagtcct gtatgccctt ttcctaacac tcacaacaaa actaactaat   7740
actaacatct cagacgctca ggaaatagaa accgtctgaa ctatcctgcc cgccatcatc   7800
ctagtcctca tcgccctccc atccctacgc atcctttaca taacagacga ggtcaacgat   7860
ccctccctta ccatcaaatc aattggccac caatggtact gaacctacga gtacaccgac   7920
tacggcggac taatcttcaa ctcctacata cttcccccat tattcctaga accaggcgac   7980
ctgcgactcc ttgacgttga caatcgagta gtactcccga ttgaagcccc cattcgtata   8040
ataattacat cacaagacgt cttgcactca tgagctgtcc ccacattagg cttaaaaaca   8100
gatgcaattc ccggacgtct aaaccaaacc actttcaccg ctacgacc ggggtatac      8160 tacggtcaat gctctgaaat ctgtggagca accacagtt tcatgcccat cgtcctagaa    8220
ttaattcccc taaaaatctt tgaaataggg cccgtattta ccctatagca cccctctac    8280 cccctctaga gcccactgta aagctaactt agcattaacc ttttaagtta agattaaga    8340 gaaccaacac ctctttacag tgaaatgcc caactaaata ctaccgtatg gcccaccata   8400 attacccca tactccttac actattcctc atcacccaac taaaaatatt aaacacaaac   8460
taccacctac ctccctcacc aaagcccata aaataaaaa attataacaa accctgagaa   8520
ccaaaatgaa cgaaaatctg ttcgcttcat tcattgcccc cacaatccta ggcctacccg   8580
ccgcagtact gatcattcta tttccccctc tattgatccc cacctccaaa tatctcatca   8640
acaaccgact aatcaccacc caacaatgac taatcaaact aacctcaaaa caaatgataa   8700
ccatacacaa cactaaagga cgaacctgat ctcttatact agtatcctta atcattttta   8760
ttgccacaac taacctcctc ggactcctgc ctcactcatt tacaccaacc acccaactat   8820
ctataaacct agccatggcc atccccttat gagcgggcac agtgattata ggctttcgct   8880
ctaagattaa aaatgcccta gcccacttct taccacaagg cacacctaca cccttatcc    8940 ccatactagt tattatcgaa accatcagcc tactcattca accaatagcc ctggccgtac   9000
gcctaaccgc taacattact gcaggccacc tactcatgca cctaattgga agcgccaccc   9060
tagcaatatc aaccattaac cttccctcta cacttatcat cttcacaatt ctaattctac   9120
```

-continued

```
tgactatcct agaaatcgct gtcgccttaa tccaagccta cgttttcaca cttctagtaa    9180
gcctctacct gcacgacaac acataatgac ccaccaatca catgcctatc atatagtaaa    9240
acccagccca tgacccctaa caggggccct ctcagccctc ctaatgacct ccggcctagc    9300
catgtgattt cacttccact ccataacgct cctcatacta ggcctactaa ccaacacact    9360
aaccatatac caatgatggc gcgatgtaac acgagaaagc ataccaag gccaccacac      9420
accacctgtc caaaaaggcc ttcgatacgg gataatccta tttattacct cagaagtttt    9480
tttcttcgca ggattttcct gagccttta ccactccagc ctagcccta ccccccaatt      9540
aggagggcac tggcccccaa caggcatcac cccgctaaat ccctagaag tcccactcct     9600
aaacacatcc gtattactcg catcaggagt atcaatcacc tgagctcacc atagtctaat    9660
agaaaacaac cgaaaccaaa taattcaagc actgcttatt acaattttac tgggtctcta    9720
ttttaccctc ctacaagcct cagagtactc gagtctccc ttcaccattt ccgacggcat     9780
ctacggctca acatttttg tagccacagg cttccacgga cttcacgtca ttattggctc     9840
aactttcctc actatctgct tcatccgcca actaatattt cactttacat ccaaacatca    9900
ctttggcttc gaagccgccg cctgatactg gcattttgta gatgtggttt gactatttct    9960
gtatgtctcc atctattgat gagggtctta ctctttttagt ataaatagta ccgttaactt  10020
ccaattaact agttttgaca acattcaaaa aagagtaata aacttcgcct taattttaat  10080
aatcaacacc ctcctagcct tactactaat aattattaca ttttgactac cacaactcaa  10140
cggctacata gaaaaatcca ccccttacga gtgcggcttc gacccatat cccccgcccg   10200
cgtcccttc tccataaaat tcttcttagt agctattacc ttcttattat ttgatctaga   10260
aattgccctc cttttaccc taccatgagc cctacaaaca actaacctgc cactaatagt  10320
tatgtcatcc ctcttattaa tcatcatcct agccctaagt ctggcctatg agtgactaca  10380
aaaggatta gactgaaccg aattggtata tagtttaaac aaaacgaatg atttcgactc   10440
attaaattat gataatcata tttaccaaat gcccctcatt tacataaata ttatactagc  10500
atttaccatc tcacttctag gaatactagt atatcgctca cacctcatat cctccctact  10560
atgcctagaa ggaataatac tatcgctgtt cattatagct actctcataa ccctcaacac  10620
ccactccctc ttagccaata ttgtgcctat tgccatacta gtctttgccg cctgcgaagc  10680
agcggtgggc ctagccctac tagtctcaat ctccaacaca tatggcctag actacgtaca  10740
taacctaaac ctactccaat gctaaaacta atcgtcccaa caattatatt actaccactg  10800
acatgacttt ccaaaaaaca cataatttga atcaacacaa ccacccacag cctaattatt  10860
agcatcatcc ctctactatt ttttaaccaa atcaacaaca acctatttag ctgttcccca  10920
acctttccct ccgacccct aacaacccc ctcctaatac taactacctg actcctaccc   10980
ctcacaatca tggcaagcca acgccactta tccagtgaac cactatcacg aaaaaaactc  11040
tacctctcta tactaatctc cctacaaatc tccttaatta taacattcac agccacagaa  11100
ctaatcatat tttatatctt cttcgaaacc acacttatcc ccaccttggc tatcatcacc  11160
cgatgaggca accagccaga acgcctgaac gcaggcacat acttcctatt ctacacccta  11220
gtaggctccc ttcccctact catcgcacta atttacactc acaacaccct aggctcacta  11280
aacattctac tactcactct cactgcccaa gaactatcaa actcctgagc caacaactta  11340
atatgactag cttacacaat agcttttata gtaaagatac ctctttacgg actccactta  11400
tgactcccta aagcccatgt cgaagccccc atcgctgggt caatagtact tgccgcagta  11460
ctcttaaaac taggcggcta tggtataata cgcctcacac tcattctcaa cccccctgaca  11520
```

```
aaacacatag cctacccctt ccttgtacta tccctatgag gcataattat aacaagctcc  11580
atctgcctac gacaaacaga cctaaaatcg ctcattgcat actcttcaat cagccacata  11640
gccctcgtag taacagccat tctcatccaa acccctgaa gcttcaccgg cgcagtcatt  11700
ctcataatcg cccacgggct tacatcctca ttactattct gcctagcaaa ctcaaactac  11760
gaacgcactc acagtcgcat cataatcctc tctcaaggac ttcaaactct actcccacta  11820
atagctttt gatgacttct agcaagcctc gctaacctcg ccttacccc cactattaac  11880
ctactgggag aactctctgt gctagtaacc acgttctcct gatcaaatat cactctccta  11940
cttacaggac tcaacatact agtcacagcc ctatactccc tctacatatt taccacaaca  12000
caatggggct cactcaccca ccacattaac aacataaaac cctcattcac acgagaaaac  12060
accctcatgt tcatacacct atcccccatt ctcctcctat ccctcaacc cgacatcatt  12120
accgggtttt cctcttgtaa atatagttta accaaaacat cagattgtga atctgacaac  12180
agaggcttac gacccttat ttaccgagaa agctcacaag aactgctaac tcatgccccc  12240
atgtctaaca acatggcttt tcaactttt aaaggataac agctatccat tggtcttagg  12300
ccccaaaaat tttggtgcaa ctccaaataa aagtaataac catgcacact actataacca  12360
ccctaaccct gacttcccta attcccccca tccttaccac cctcgttaac cctaacaaaa  12420
aaaactcata cccccattat gtaaaatcca ttgtcgcatc cacctttatt atcagtctct  12480
tccccacaac aatattcatg tgcctagacc aagaagttat tatctcgaac tgacactgag  12540
ccacaaccca aacaacccag ctctccctaa gcttcaaact agactacttc tccataatat  12600
tcatccctgt agcattgttc gttacatggt ccatcataga attctcactg tgatatataa  12660
actcagaccc aaacattaat cagttcttca aatatctact catcttccta attaccatac  12720
taatcttagt taccgctaac aacctattcc aactgttcat cggctgagag ggcgtaggaa  12780
ttatatcctt cttgctcatc agttgatgat acgcccgagc agatgccaac acagcagcca  12840
ttcaagcaat cctatacaac cgtatcggcg atatcggttt catcctcgcc ttagcatgat  12900
ttatcctaca ctccaactca tgagacccac aacaaatagc ccttctaaac gctaatccaa  12960
gcctcacccc actactaggc ctcctcctag cagcagcagg caaatcagcc caattaggtc  13020
tccaccctg actcccctca gccatagaag gccccacccc agtctcagcc ctactccact  13080
caagcactat agttgtagca ggaatcttct tactcatccg cttccacccc ctagcagaaa  13140
atagcccact aatccaaact ctaacactat gcttaggcgc tatcaccact ctgttcgcag  13200
cagtctgcgc ccttacacaa aatgacatca aaaaaatcgt agccttctcc acttcaagtc  13260
aactaggact cataatagtt acaatcggca tcaaccaacc acacctagca ttcctgcaca  13320
tctgtacca cgccttcttc aaagccatac tatttatgtg ctccgggtcc atcatccaca  13380
accttaacaa tgaacaagat attcgaaaaa taggaggact actcaaaacc atacctctca  13440
cttcaacctc cctcaccatt ggcagcctag cattagcagg aatacctttc ctcacaggtt  13500
tctactccaa agaccacatc atcgaaaccg caaacatatc atacacaaac gcctgagccc  13560
tatctattac tctcatcgct acctccctga caagcgccta tagcactcga ataattcttc  13620
tcaccctaac aggtcaacct cgcttcccca cccttactaa cattaacgaa ataaccccca  13680
ccctactaaa ccccattaaa cgcctggcag ccggaagcct attcgcagga tttctcatta  13740
ctaacaacat ttccccgca tccccttcc aaacaacaat cccctctac ctaaaactca  13800
cagccctcgc tgtcactttc ctaggactc taacagccct agacctcaac tacctaacca  13860
```

-continued

```
acaaacttaa aataaaatcc ccactatgca catttattt ctccaacata ctcggattct    13920
accctagcat cacacaccgc acaatcccct atctaggcct tcttacgagc caaaacctgc    13980
ccctactcct cctagaccta acctgactag aaaagctatt acctaaaaca atttcacagc    14040
accaaatctc cacctccatc atacctcaa cccaaaaagg cataattaaa ctttacttcc     14100
tctctttctt cttcccactc atcctaaccc tactcctaat cacataacct attcccccga    14160
gcaatctcaa ttacaatata tacaccaaca aacaatgttc aaccagtaac tactactaat    14220
caacgcccat aatcatacaa agcccccgca ccaataggat cctcccgaat caaccctgac    14280
ccctctcctt cataaattat tcagcttcct acactattaa agtttaccac aaccaccacc    14340
ccatcatact ctttcaccca cagcaccaat cctacctcca tcgctaaccc cactaaaaca    14400
ctcaccaaga cctcaacccc tgaccccat gcctcaggat actcctcaat agccatcgct    14460
gtagtatatc caaagacaac catcattccc cctaaataaa ttaaaaaaac tattaaaccc    14520
atataacctc ccccaaaatt cagaataata acacacccga ccacaccgct aacaatcaat    14580
actaaacccc cataaatagg agaaggctta gaagaaaacc ccacaaaccc cattactaaa    14640
cccacactca acagaaacaa agcatacatc attattctcg cacggactac aaccacgacc    14700
aatgatatga aaaccatcg ttgtatttca actacaagaa caccaatgac cccaatacgc     14760
aaaactaacc ccctaataaa attaattaac cactcattca tcgacctccc caccccatcc    14820
aacatctccg catgatgaaa cttcggctca ctccttggcg cctgcctgat cctccaaatc    14880
accacaggac tattcctagc catgcactac tcaccagacg cctcaaccgc cttttcatca    14940
atcgcccaca tcactcgaga cgtaaattat ggctgaatca tccgctacct tcacgccaat    15000
ggcgcctcaa tattctttat ctgcctcttc ctacacatcg ggcgaggcct atattacgga    15060
tcatttctct actcagaaac ctgaaacatc ggcattatcc tcctgcttgc aactatagca    15120
acagccttca taggctatgt cctcccgtga ggccaaatat cattctgagg ggccacagta    15180
attacaaact tactatccgc catcccatac attgggacag acctagttca atgaatctga    15240
ggaggctact cagtagacag tcccaccctc acacgattct ttacctttca cttcatcttg    15300
cccttcatta ttgcagccct agcaacactc cacctcctat tcttgcacga acgggatca     15360 aacaacccc taggaatcac ctcccattcc gataaaatca ccttccaccc ttactacaca    15420
atcaaagacg ccctcggctt acttctcttc cttctctcct taatgacatt aacactattc    15480
tcaccagacc tcctaggcga cccagacaat tataccctag ccaacccctt aaacaccct     15540 ccccacatca gcccgaatg atatttccta ttcgcctaca caattctccg atccgtccct     15600
aacaaactag gaggcgtcct tgccctatta ctatccatcc tcatcctagc aataatcccc    15660
atcctccata tatccaaaca acaaagcata atatttcgcc cactaagcca atcactttat    15720
tgactcctag ccgcagacct cctcattcta acctgaatcg gaggacaacc agtaagctac    15780 cctttacca tcattggaca agtagcatcc gtactatact tcacaacaat cctaatccta    15840
ataccaacta tctccctaat tgaaaacaaa atactcaaat gggcctgtcc ttgtagtata    15900
aactaataca ccagtcttgt aaaccggaga tgaaaacctt tttccaagga caaatcagag    15960
aaaaagtctt taactccacc attagcaccc aaagctaaga ttctaattta aactattctc    16020
tgttctttca tggggaagca gatttgggta ccacccaagt attgactcac ccatcaacaa    16080
ccgctatgta tttcgtacat tactgccagc caccatgaat attgtacggt accataaata    16140
cttgaccacc tgtagtacat aaaaacccaa tccacatcaa acccctcc ccatgcttac      16200 aagcaagtac agcaatcaac cctcaactat cacacatcaa ctgcaactcc aaagccaccc    16260
```

```
ctcacccact aggataccaa caaacctacc caccottaac agtacatagt acataaagcc    16320
atttaccgta catagcacat tacagtcaaa tcccttctcg tccccatgga tgaccccct     16380 cagatagggg tcccttgacc accatcctcc gtgaaatcaa tatcccgcac aagagtgcta    16440
ctctcctcgc tccgggccca taacacttgg gggtagctaa agtgaactgt atccgacatc    16500
tggttcctac ttcagggtca taaagcctaa atagcccaca cgttcccctt aaataagaca    16560
tcacgatg                                                             16568

<210> SEQ ID NO 2
<211> LENGTH: 23
<212> TYPE: DNA
<213> ORGANISM: Homo sapiens

<400> SEQUENCE: 2
gtatttggat gtcagaaaca ctt                                            23

<210> SEQ ID NO 3
<211> LENGTH: 19
<212> TYPE: DNA
<213> ORGANISM: Homo sapiens

<400> SEQUENCE: 3
acttcagggt cataaagcc                                                 19

<210> SEQ ID NO 4
<211> LENGTH: 23
<212> TYPE: DNA
<213> ORGANISM: Homo sapiens

<400> SEQUENCE: 4
gtatttggat gtcagaaaca ctt                                            23

<210> SEQ ID NO 5
<211> LENGTH: 19
<212> TYPE: DNA
<213> ORGANISM: Homo sapiens

<400> SEQUENCE: 5
acttcagggc cataaagcc                                                 19

<210> SEQ ID NO 6
<211> LENGTH: 21
<212> TYPE: DNA
<213> ORGANISM: Homo sapiens

<400> SEQUENCE: 6
acccgcgtcc gcgccatggc c                                              21

<210> SEQ ID NO 7
<211> LENGTH: 21
<212> TYPE: DNA
<213> ORGANISM: Homo sapiens

<400> SEQUENCE: 7
acccgcgtcc tcgccatggc c                                              21

<210> SEQ ID NO 8
<211> LENGTH: 8
<212> TYPE: DNA
<213> ORGANISM: Homo sapiens
```

```
<400> SEQUENCE: 8 taaccata                                                                    8

<210> SEQ ID NO 9
<211> LENGTH: 9
<212> TYPE: DNA
<213> ORGANISM: Homo sapiens

<400> SEQUENCE: 9 tctcttacc                                                                   9

<210> SEQ ID NO 10
<211> LENGTH: 10
<212> TYPE: DNA
<213> ORGANISM: Homo sapiens

<400> SEQUENCE: 10
cacactacta                                                                 10

<210> SEQ ID NO 11
<211> LENGTH: 9
<212> TYPE: DNA
<213> ORGANISM: Homo sapiens

<400> SEQUENCE: 11 tttaaccag                                                                   9
```